United States Patent [19]

Loesch-Fries et al.

[11] Patent Number: 5,316,930
[45] Date of Patent: May 31, 1994

[54] VIRUS RESISTANT PLANTS HAVING ANTISENSE RNA

[75] Inventors: L. Sue Loesch-Fries; Nancy J. Eagan, both of Madison, Wis.; Donald J. Merlo, Midland, Mich.; Carol Alexandrescu, Madison, Wis.

[73] Assignee: Pioneer Hi-Bred International, Inc., Johnston, Iowa

[21] Appl. No.: 293,905

[22] Filed: Jan. 5, 1989

Related U.S. Application Data

[63] Continuation-in-part of Ser. No. 847,425, Apr. 2, 1986, abandoned.

[51] Int. Cl.$^5$ .................... C12N 15/00; C12N 5/00; A01H 1/04; C12R 1/41; C07H 21/04
[52] U.S. Cl. ........................ 435/172.3; 435/240.4; 435/252.3; 800/205; 800/250; 536/23.2; 536/24.5
[58] Field of Search ............... 435/172.3, 252.3, 252.2, 435/240.4, 320; 800/1, 205, 250; 536/27, 24.5, 23.2

[56] References Cited

FOREIGN PATENT DOCUMENTS

| | | |
|---|---|---|
| 0126546 | 11/1984 | European Pat. Off. |
| 0194809 | 9/1986 | European Pat. Off. |
| 8605516 | 9/1986 | European Pat. Off. |
| 0223399 | 5/1987 | European Pat. Off. |
| 0223452 | 5/1987 | European Pat. Off. |
| 8703451 | 6/1987 | European Pat. Off. |
| 0240208 | 10/1987 | European Pat. Off. |
| 2148302 | 5/1985 | United Kingdom. |

OTHER PUBLICATIONS

Loesch-Fries et al. (1986) J. Cell. Biochem., No. 10, part C, (Abstract) abstract No. 108, p. 41.
Schieder, O. (Jan. 1987) Chem. Abstracts, 106:1, abstract No. 1346m, p. 134.
Dean, P. D. G. (1985) Proc. of Biotech 1985 Europe, Geneva, May 1985, vol. 1, Online Publications, Pinner, UK, pp. 301-309.
Pines, O. and Inouye, M. (1986) Trends Genet 2:284-287.
Hirashima A. et al. (1986) Proc. Natl. Acad. Sci. USA 83:7726-7730.
Agrios, In: Plant Pathology, 2:585, Academic Press, Inc., New York (1978).
Ahlquist et al., "Multicomponent RNA Plant Virus Infection Derived from Cloned Viral cDNA," Proc. Natl. Acad. Sci. USA 81:7066-7070 (1984).
Barker et al., "Complete Nucleotide Sequence of Alfalfa Mosaic Virus RNA3," Nucl. Acids Res. 11:2881-2891 (1983).
Barton et al., "Regeneration of Intact Tobacco Plants Containing Full Length Copies of Genetically Engineered T-DNA " . . . Cell 32:1033-1043 (1983).
Bevan et al., "Expression of Tobacco Mosaic Virus Coat Protein by a Cauliflower Mosaic Virus Promoter in Plants . . . " EMBO J. 4:1921-1926 (1985).
Bevan et al., "A Chimaeric Antibiotic Resistance Gene as a Selectable Marker for Plant Cell Transformation," Nature 304:184-187 (1983).
Brederode et al., "Complete Nucleotide Sequence of Alfalfa Mosaic Virus RNA4," Nucl. Acids Res. 8:2213-2223 (1980).
Chang et al., "Gene Expression from Both Intronless and Intron-containing Rous Sarcoma Virus Clones is . . . ," Mol. Cell Biol. 5(9):2341-2348 (1985).

(List continued on next page.)

*Primary Examiner*—David T. Fox
*Attorney, Agent, or Firm*—Sterne, Kessler, Goldstein & Fox

[57] ABSTRACT

The making of plant cells which contain antisense RNA (aRNA) complementary to the mRNA of an alfalfa mosaic virus is disclosed. Construction of such aRNA genes and transformation thereof into plant cells is also taught. Such cells are relatively resistant to infection by the target virus when compared with cells not containing the aRNA. Methods and DNA molecules useful for producing plant cells containing said aRNA are also disclosed.

60 Claims, 1 Drawing Sheet

OTHER PUBLICATIONS

Chilton et al., "Stable Incorporation of Plasmid DNA into Higher Plant Cells: The Molecular Basis of Crown Gall Tumorigenesis," Cell 11:263–271 (1977).

Chilton et al., "Tailoring the Agrobacterium T. Plasmid as a Vector for Plant Genetic Engineering," Stadler Symposium 13:39–52 (1981).

Coleman et al., "A Novel Immune System Against Bacteriophage Infection Using Complementary RNA (micRNA)," Nature 315:601–603 (1985).

Cornelissen et al., "Complete Nucleotide Sequence of Alfalfa Mosaic Virus RNA1," Nucl. Acids Res. 11:1253–1265 (1983).

Cornelissen et al., "Complete Nucleotide Sequence of Alfalfa Mosaic Virus RNA2," Nucl. Acids Res. 11:3019–3025 (1983).

de Zoeten et al., "Understanding Generates Possibilities," Letter to the Editor, Phytopathology 65(3):221–222 (1975).

Fraley et al., "Expression of Bacterial Genes in Plant Cells," Proc. Natl. Acad. Sci. USA 80:4803–4807 (1983).

Goodman et al., "Gene Transfer in Crop Improvement," Science 236:48–54 (1987).

Hamilton, "Defenses Triggered by Previous Invaders: Viruses," Plant Disease—An Advanced Treatise, vol. v, pp. 279–303 (1980), Ed. Horsfall and Cowling, Academic Press, New York.

Hepburn et al., "The Effect of Right Terminal Repeat Deletion on the Oncogenicity of the T-Region of pTiT37," Plant Mol. Biol. 5:3–11 (1985).

Hernalsteens et al., "The Agrobacterium Tumefaciens Ti Plasmid as a Host Vector System for Introducing Foreign DNA in Plant Cells," Nature 287:654–656 (1980).

Herrera-Estrella et al., "Chimeric Genes as Dominant Selectable Markers in Plant Cells," EMBO J. 2(6):987–995 (1983).

Herrera-Estrella et al., "Expression of Chimeric Genes Transferred into Plant Cells Using a Ti-Plasmid-Derived Vector," Nature 303:209–213 (1983).

Hoekema et al., "Delivery of T-DNA from the Agrobacterium Tumefaciens Chromosome into Plant Cells," EMBO J. 3(11):2485–2490 (1984).

Horsch et al., "Inheritance of Functional Foreign Genes in Plants," Science 223:496–498 (1984).

Izant et al., "Inhibition of Thymidine Kinase Gene Expression by Anti-Sense RNA: A Molecular Approach to Genetic Analysis," Cell 36:1007–1015 (1984).

Izant et al., "Constitutive and Conditional Suppression of Exogenous and Endogenous Genes by Anti-Sense RNA," Science 229:345–352 (1985).

Kemp et al., "Agrobacterium-Mediated Transfer of Foreign Genes into Plants," Genetic Engineering: Applications to Agriculture, Beltsville Symposium 7, pp. 215–228 (1982).

Koziel et al., "A Cauliflower Mosaic Virus Promoter Directs Expression of Kanamycin Resistance in Morphogenic . . . ," J. Mol. Appl. Genet. 2(6):546–562 (1984).

Loesch-Fries et al., "Expression of Alfalfa Mosaic Virus RNA4 in Transgenic Plants Confers Virus Resistance," EMBO J. 6(7):1845–1851 (1987).

Loesch-Fries et al., "Human Leukocyte Interferon Does Not Inhibit Alfalfa Mosaic Virus in Protoplasts or Tobacco Issue," Virology 143:626–629 (1985).

Meshi et al., "Nucleotide Sequence of a Cloned cDNA Copy of TMV (Cowpea Strain) RNA, Including the Assembly Origin . . . ," Mol. Gen. Genet. 184:20–25 (1981).

Meshi et al., "Molecular Cloning of the Complementary DNA Copies of the Common and Cowpea Strains of Tobacco Mosaic Virus RNA," Virology 118:64–75 (1982).

Nelson et al., "RNA Complementary to Alfalfa Mosaic Virus RNA4 is Not Translated in vitro," Intervirology 27:172–176 (1987).

Palukaitis et al., "A Model to Explain the 'Cross Protection' Phenomenon Shown by Plant Viruses and Viroids," pp. 420–429 In: Plant-Microbe Interactions, vol. 1 Kosuge et al., eds. (1984).

(List continued on next page.)

OTHER PUBLICATIONS

Rubin, "Genetic Studies on the Role of Octopine T-DNA Border Regions in Crown Gall Tumor Formation," Mol. Gen. Genet. 202:312-320 (1986).

Sanford et al., "The Concept of Parasite-Derived Resistance—Deriving Resistance Genes from the Parasite's Own Genome," J. Theor. Biol. 113:395-405 (1985).

Sequeira, "Cross Protection and Induced Resistance: Their Potential for Plant Disease Control," Trends Biotech. 2:25-29 (1984).

Shaw et al., "The Right Hand Copy of the Nopaline Ti-plasmid 25 bp Repeat is Required for Tumor Formation," Nucl. Acids Res. 12:6031-6041 (1984).

Stebbing, "The Design of Antiviral Agents Based on Strategic Sequences in Viral RNA and AntiViral Effects of Single Stranded Polynucleotides," Pharmac. Ther. 6:291-332 (1979).

Travers, "Regulation by Anti-sense RNA," Nature 311:410 (1984).

Weintraub et al., "Anti-sense RNA as a Molecular Tool for Genetic Analysis," Trends Genet. 1:22-25 (1985).

Yamada et al., "Regeneration of Rice Plants from Protoplasts," Rice Genet. Newsletter 2:94-95 (1985).

Zambryski et al., "Ti Plasmid Vector for the Introduction of DNA into Plant Cells Without Alteration of Their Normal Regeneration Capacity," EMBO J. 2(12):2143-2150 (1983).

pGEMA3L

VIRUS RESISTANT PLANTS HAVING ANTISENSE RNA

CROSS-REFERENCE TO RELATED APPLICATIONS

This application is a continuation-in-part of copending application Ser. No. 847,425, filed Apr. 2, 1986, now abandoned, which is incorporated herein by reference.

FIELD OF THE INVENTION

The present invention is in the fields of genetic engineering and plant husbandry, and especially provides a means for producing a virus resistant plant by transforming a plant to contain a plant-expressible foreign gene directing synthesis of RNA complementary to a viral mRNA. Also provided are plant-transforming prokaryotic plasmid vectors carrying such plant-expressible RNA and plant cells transformed by such a vector.

BACKGROUND OF THE INVENTION

Overview of Agrobacterium

Virulent strains of the gram-negative genus Agrobacterium harbor large plasmids known as Ti (tumor- or transformation-inducing) plasmids (pTi) in *A. tumefaciens* and Ri (root-inducing) plasmids (pRi) in *A. rhizogenes*, often classified by the opine which they catabolize or cause to be synthesized. Ti and Ri plasmids both contain DNA sequences, known as T-DNA (transferred-DNA), which in tumors are found to be integrated into the genome of the host plant. Several T-DNA genes are under control of T-DNA promoters which resemble canonical eukaryotic promoters in structure. These plasmids also carry genes outside the T-DNA region. Ti and Ri plasmids are for many purposes functionally equivalent.

Reviews of Agrobacterium-caused disease, plant transformation, genetic engineering, and gene expression include those by, or found in, Merlo, D. J. (1982) Adv. Plant Pathol. 1:139–178; Ream, L. W. and Gordon, M. P. (1982) Science 218:854–859; Bevan, M. W. and Chilton, M-D. (1982) Ann. Rev. Genet. 16:357–384; Kahl, G. and Schell, J. (1982) *Molecular Biology of Plant Tumors*; Barton, K. A. and Chilton, M-D. (1983) Meth. Enzymol. 101:527–539; Depicker, A. et al. (1983) in *Genetic Engineering of Plants: an Agricultural Perspective*, Kosuge T et al. (eds.), pp 143–176; Caplan, A. et al. (1983) Science 222:815–821; Hall, T. C. et al., European Patent application 126,546; Binns, A. N. (1984) Oxford Surveys Plant Mol. Cell Biol. 1:130–160; Hall, T. C. (1985) Oxford Surveys Plant Mol. Biol. 2:329–338; Hooykaas, P. J. J. and Schilperoort, R. A. (1985) Trends Biochem. Sci. 10:307–309; Thomas, T. L. and Hall, T. C. (1985) Bioassays 3: 149-153; Weissbach, A. and Weissbach, H. (eds.) (1986) Meth. Enzymol. 118: (see especially Rogers et al. pp 627–640); Puhler, A. (ed.) (1983) *Molecular Genetics of the Bacteria-Plant Interaction*; and Schilperoort, R. A. (1984) in *Efficiency in Plant Breeding* (Proc. 10th Congr. Eur. Assoc. Res. Plant Breeding), Lange, W. et al. (eds.), pp 251–285.

Transformation of Plants by Agrobacterium

Plant cells can be transformed by Agrobacterium by several methods well-known in the art. For a review of recent work, see Syono, K. (1984) Oxford Surveys Plant Mol. Cell Biol. 1:217–219.

The infection of plant tissue by Agrobacterium is a simple technique well-known to those skilled in the art. Typically after being wounded, a plant is inoculated with a suspension of the bacteria. Alternatively, tissue pieces are inoculated, e.g., leaf disks (Horsh, R. B. et al. (1985) Science 227:1229–1231). After induction with wild-type Agrobacterium, the tumors are capable of phytohormone-independent growth. Traditional inoculation and culture techniques may be modified for use of disarmed T-DNA vectors incapable of hormone-independent growth (e.g., see Zambryski, P. et al. (1984) in *Genetic Engineering, Principles, and Methods*, 6, Hollaender, A. and Setlow, J. (eds.), pp 253–278).

Agrobacterium is also capable of infecting isolated cells, cells grown in culture, callus cells, and isolated protoplasts (e.g., Fraley, R. T. et al. (1984) Plant Mol. Biol. 3:371–378; Fraley, R. T. and Horsch, R. B. (1983) in *Genetic Engineering of Plants: an Agricultural Perspective*, Kosuge, T. et al. (eds.), pp 177–194; Muller, A. et al. (1983) Biochem. Biophys. Res. Comm. 123:458–462). The transformation frequency of inoculated callus pieces can be increased by addition of an opine precursor (Cello, L. M. and Olsen, W. L., U.S. Pat. No. 4,459,355).

The host range of crown gall pathogenesis may be influenced by T-DNA-encoded functions such as onc genes (Hoekema, A. et al. (1984) J. Bacteriol. 158:383–385; Hoekema, A. et al. (1984) EMBO J. 3:3043–3047; Buchholz, W. C. and Thomasshow, M. F. (1984) 160:327–332; Yanofsky, M. (1985) Mol. Gen. Genet. 201:237–246). Vir genes also affect host range (Yanofsky, supra). Ausich, R. L., European Patent Application 108,580, reports transfer of T-DNA from *A. tumefaciens* to green algal cells, and expression therein of ocs and Tn5 kanamycin resistance genes. Hooykaas-van Slogteren, G. M. S. et al. (1984) Nature 311:763–764, and Hernalsteens, J-P. et al. (1984) EMBO J. 3:3039–3041, have demonstrated transformation of monocot cells by Agrobacterium without the customary tumorigenesis.

T-DNA, disarmed T-DNA, and functional foreign genes of transformed plants are usually transmitted through meiosis to progeny seemingly unaltered in a dominant, closely-linked, Mendelian fashion (e.g., see Horsch, R. B. et al. (1984) Science 223:496–498; Tepfer, D. (1984) Cell 37:959–967; DeBlock, M. et al. (1984) EMBO J. 3:1681–1689; Wostemeyer, A. et al. (1984) Mol. Gen. Genet. 194:500–507; Wallroth, M. et al. (1986) Mol. Gen. Genet. 202:6–15). Two unlinked T-DNAs can transform a single cell and, after plant regeneration, segregate in the F1 generation (de Framond, A. J. et al. (1986) Mol. Gen. Genet. 202:125–131).

Ti Plasmid DNA

T-DNA is often integrated (i.e., inserted) into host DNA at multiple sites in the nucleus. Flanking plant DNA may be either repeated or low copy number sequences. Integrated T-DNA can be found in either direct or inverted tandem arrays and can be separated by spacers. T-DNA can also transform chloroplasts (De Block, M. et al. (1985) EMBO J. 4:1367–1372; see review by Flavell, R. B. (1985) Bioassays 3:177–178).

The complete sequence of the T-DNA of an octopine-type plasmid found in ATCC 15955, pTi15955, has been reported (Barker, R. F. et al. (1983) Plant Mol. 2:335–350) as has the $T_L$ region of pTiAch5 (Gielen, J. et al. (1984) EMBO J. 3:835–846). Published T-DNA genes do not contain introns. Sequences resembling canonical eukaryotic promoter elements and polyadenylation sites can be recognized.

Octopine Ti plasmids carry an ocs gene which encodes octopine synthase (lysopine dehydrogenase). Koncz, C. et al. (1983) EMBO J. 2:1597-1603 provides a functional analysis of ocs. Dhaese, P. et al. (1983) EMBO J. 2:419-426, reported the utilization of various polyadenylation sites by "transcript 7" (ORF3 of Barker, R. et al. supra) and ocs. The presence of the enzyme octopine synthase within a tissue can protect that tissue from the toxic effect of various amino acid analogs, e.g., aminoethyl cysteine (Dahl, G. A. and Tempe, J. (1983) Theor. Appl. Genet. 66:233-239; Koziel, M. G. et al. (1984) J. Mol. Appl. Genet. 2:549-562).

Nopaline Ti plasmids encode the nopaline synthase gene (nos) (sequenced by Depicker, A. et al. (1982) J. Mol. Appl. Genet. 1:561-573). Shaw, C. H. et al. (1984) Nucl. Acids Res. 12:7831-7846, provides a functional analysis of nos. Genes equivalent to tms and tmr have been identified on a nopaline-type plasmid (Willmitzer, L. et al. (1983) Cell 32:1045-1056).

Ti and Ri plasmid genes outside of the T-DNA region include the vir genes, which when mutated result in an avirulent Ti plasmid. The vir genes function in trans, being capable of causing the transformation of plant cells with T-DNA of a different plasmid type and physically located in another plasmid. Such arrangements are known as binary systems and the T-DNA bearing plasmids are generally known as micro-Ti plasmids. Disclosed binary systems and micro-Ti plasmids include the following: Hoekema, A. et al. (1985) Plant Mol. Biol. 5:85-89; Deblaere, R. et al. (1985) Nucl. Acids Res. 13:4777-4788; van den Elzen, P. et al. (1985) Plant Mol. Biol. 5:149-154; Anderson, D. M., U.S. Pat. No. 4,536,475; de Framond, A. J. et al. (1983) Biotechnol. 1:262-269; Hoekema, A. et al. (1983) Nature 303:179-180; Hille, J. et al. (1984) J. Bacteriol. 158:754-756; Hoekema, A. et al. (1984) J. Bacteriol. 158:383-385; An, G. et al. (1985) EMBO J. 4:277-284; Anderson, D. M., U.S. Pat. No. 4,536,475; Klee, H. J. et al. (1985) Biotechnol. 3:637-642); de Framond, A. J. et al. (1986) Mol. Gen. Genet. 202:125-131; Dahl, G. A. et al., European Patent Application 140,556; and Bevan, M, (1984) Nucl. Acids Res. 12:8711-8721. T-DNA need not be on a plasmid to transform a plant cell; chromosomally located T-DNA is functional (Hoekema, A. et al. (1984) EMBO J. 3:2485-2490). T-DNA has direct repeats of about 25 base pairs associated with the left and right borders, i.e., with the T-DNA/plant DNA junctions, which may be involved in either transfer from Agrobacterium or integration into the host genome. Ti plasmid-determined characteristics have been reviewed by Merlo, supra (see especially Table II), and Ream and Gordon, supra.

Foreign Gene Expression

A gene encoding bean phaseolin has been transferred into and expressed in sunflower tumors (Murai, N. et al. (1983) Science 222:476-482) The phaseolin gene was expressed at a high level in developing tobacco seeds (Sengupta-Gopalan, C. et al. (1985) Proc. Natl. Acad. Sci. USA 82:3320-3324). Similar results have been observed with a homologous gene, soybean beta-conglycinin (Beachy, R. N. et al. (1985) EMBO J. 4:3047-3053). A gene for the endosperm protein zein, from the monocot *Zea mays*, is transcribed in sunflower callus (Matzke, M. A. et al. (1984) EMBO J. 3:1525-1531). Expression of a pea RuBP-Case small subunit gene is light-regulated in transformed petunia cells; the pea small subunit protein produced is correctly processed and sequestered within chloroplasts (Broglie, R. et al. (1984) Science 224:838-843). Sequences involved in this light-inducibility and those needed for maximal expression have been identified (Morelli, G. et al. (1985) Nature 315:200-204; Nagy, F. et al. (1985) EMBO J. 4:3063-3068; Timko, M. P. et al. (1985) Nature 318:579-582). Expression of a wheat chlorophyll a/b binding protein gene is light-regulated and organ-specific in transformed tobacco plants (Lamppa, G. et al. (1985) Nature 316:750-752). A soybean heat shock gene is thermoinducible in sunflower tissue (Schoffl, F. and Baumann, G. (1985) EMBO J. 4:1119-1124). A *Drosophila melanogaster* heat shock promoter is similarly functional in tobacco tissue (Spena, A. et al. (1985) EMBO J.4:2739-2743).

Chimeric Genes Having T-DNA Promoters

The nos promoter can drive expression of drug resistance structural genes useful for selection of transformed plant cells. Resistance genes have been identified for kanamycin (Bevan, M. W. et al. (1983) Nature 304:184-187; Fraley, R. T. et al. (1983) Proc. Natl. Acad. Sci. USA 80:4803-4807; Herrera-Estrella, L. et al. (1983) EMBO J. 2:987-995), methotrexate (Herrera-Estrella, et al. supra), chloramphenicol (Herrera-Estrella, L. et al. (1983) Nature 303:209-213), hygromycin B (van den Elzen, P. J. M. et al. (1985) Plant Mol. Biol. 5:299-302). Helmer, G. et al. (1984) Biotechnol. 2:520-527, have created a fusion gene having the promoter and 5'-end of the structural gene of nos fused to *E. coli* beta-galactosidase (lacZ) sequences. Plant tissues transformed with this screenable marker may be recognized by a characteristic color when grown on the appropriate chromogenic substrate.

Fusion protein genes between the ocs structural gene, which also provided promoters, and structural genes for hygromycin B resistance and phaseolin have been created and are functional (Waldron, C. et al. (1985) Plant Mol. Biol. 5:103-108; Murai, N. et al. (1983) Science 222:476-482). A glyphosate resistance gene behind the ocs promoter has been constructed (Comai, L. et al. (1985) Nature 317:741-744).

Promoters for octopine $T_L$ genes ORF24 and ORF25 can also drive structural gene expression (Velten, J. et al. (1984) EMBO J. 3:2723-2730; Velten, J. and Schell, J. (1985) Nucl. Acids Res. 13:6981-6998; Gelvin, S. B. et al. (1985) Mol. Gen. Genet. 199:240-248; Comai, L. et al. (1985) Nature 317:741-744).

Chimeric Genes Having Plant Promoters

A chimeric RuBP-Case small subunit/kanamycin resistance protein was translocated into a chloroplast (Van den Broeck, G. et al. (1985) Nature 313:358-363). The gene encoding this protein carries a promoter that confers light-inducible expression in callus to kanamycin through expression of the kanamycin resistance gene (Herrera-Estrella, L. et al. (1984) Nature 310:115-120; Facciotti, D. et al. (1985) Biotechnol. 3:241-246). A chalcone synthase promoter also drove light-inducible expression of a kanamycin resistance gene (Kaulen, H. et al. (1986) EMBO J. 5:1-8). Chlorophyll a/b binding protein promoters have been used to drive expression of ocs and kanamycin resistance structural genes (Jones, J. D. G. et al. (1985) EMBO J.

4:2411–2418; Simpson, J. et al. (1985) EMBO J. 4:2723–2729).

Chimeric Genes Having Viral Promoters

A kanamycin resistance gene under control of a cauliflower mosaic virus (CaMV) promoter was expressed in plant cells transformed by T-DNA (Koziel, M. G. et al. (1984) J. Mol. Appl. Genet. 2:549–562). A methotrexate resistance gene behind the CaMV 35S promoter conferred methotrexate resistance (Brisson, N. et al. (1984) Nature 310:511–514). Tobacco mosaic virus coat protein has been expressed in transformed tobacco tissue under control of a CaMV promoter (Bevan, M. W. et al. (1985) EMBO J. 4:1921–1926). Odell, J. T. et al. (1985) Nature 313:810–812, have mapped sequences of the CaMV 35S promoter needed for transcription.

Transformation of Plants without Agrobacterium

Direct transfer of DNA into plant cells has been recently reviewed (Jones, M. G. K. (1985) Nature 317:579–580; Potrykus, I. et al. (1985) Plant Mol. Biol. Rep. 3:117–128; Howe, C. (1985) Trends Genet. 1:38–39; Paszkowski, J. and Saul, M. W. (1986) Methods Enzymol. 118:659–668; Power, J. B. et al. (1986) Methods Enzymol. 118:578–594). Both dicot and monocot cells can by directly transformed by kanamycin-selectable marker genes under control of either a nos or CaMV promoter (Paskowski, J. et al. (1984) EMBO J. 3:2717–2722; Gardner, R. C. et al. (1984) Plant Mol. Biol. Rep. 2:3–8; Hain, R. et al. (1985) Mol. Gen. Genet. 199:161–168; Potrykus, I. et al. (1985) Mol. Gen. Genet. 199:183–188; Lorz, H. et al. (1985) Mol. Gen. Genet. 199:178–182; Shillito, R. D. et al. (1985) Biotechnol. 3:1099–1103; Meyer, P. et al. (1985) Mol. Gen. Genet. 201:513–518). Distinct DNA molecules can be co-transformed into a plant cell; it is advantageous that one DNA in the mixture carries a selectable marker (Peerbolte, R. et al. (1985) Plant Mol. Biol. 5:235–246). Descendants of plants regenerated from such transformed cells inherit the transformed hybrid gene as a single, dominant, Mendelian trait (Potrykus et al. (1985) Mol. Gen. Genet. supra).

CaMV has proven useful as a plant transformation vector (Brisson, N. et al. (1984) Nature 310:511–514; Brisson, N. and Hohn, T. (1986) Methods Enzymol. 118:659–668). Bromegrass mosaic virus (BMV), an RNA virus, can also be used in plants to express foreign structural genes (French, R. et al. (1986) Science 231:1294–1297).

Electroporation has proven useful for introducing chimeric genes into plant cells in a transient expression system (Fromm, M. et al. (1985) Proc. Natl. Acad. Sci. USA 82:5824–5828) and for stable transformation of maize cells (Fromm, M. E. et al. (1986) Nature 319:791–793).

Cells can take up DNA surrounded by membranes. DNA, including pTi DNA, may be introduced via liposomes (e.g., Deshayes, A. et al. (1985) EMBO J. 4:2731–2737) or by fusion of plant and bacterial cells after removal of their respective cell walls (e.g., Hain, R. et al. (1984) Plant Cell Rep. 3:60–64). Plant protoplasts can take up cell wall delimited Agrobacterium cells, and integrated T-DNA is stably transmitted to tissue regenerated from these protoplasts.

DNA can be stably integrated into a genome after microinjection (Crossway, A. et al. (1986) Mol. Gen. Genet. 202:179–185).

DNA can also be stably integrated into a plant genome following introduction of DNA into cells carried on small particles, usually made of gold or tungsten. Cells are bombarded by these DNA-coated microprojectiles that are accelerated via an explosive discharge (Klein, T. M. et al. (1987) Nature 327:70–73), or via an electrical discharge (McCabe, D. E. et al. (1988) Biotechnology 6:923–936). Microprojectile bombardment for the introduction of DNA is considered applicable to all plant species.

Introduction of DNA into plant cells during fertilization or pollination has been reported for corn and cotton by Ohta, Y. (1986) Methods Enzymol. 101:433–481, respectively.

Overview of AMV

Alfalfa mosaic virus (AMV) is one class of plant viruses having a tripartite, single-stranded, plus-stranded RNA genome. The genome (excluding the subgenomic RNA molecules) is segmented into three RNA molecules. This class includes: the alfalfa mosaic virus (AMV) group, the ilarviruses, the bromoviruses, the cucumoviruses, and the hordeiviruses (van Vloten-Doting, L. et al. (1981) Interviol. 15:198–203; Matthews, R. E. F. (1982) *Classification and Nomenclature of Viruses*). The genome segments are separately encapsidated in bacilliform particles of different lengths. Besides the three genomic RNA components (RNA1, RNA2, and RNA3), a fourth subgenomic RNA (RNA4) is found in virus preparations. A mixture of the three genome RNAs together with a small amount of coat protein or its messenger, RNA4 (Bol, J. F. et al. (1971) Virol. 46:73–85), is required to initiate infection.

The complete sequence of AMV RNA4 has been disclosed (Brederode, F. T. et al. (1980) Nucl. Acids Res. 8:2213–2223). RNA4 is 881 nucleotides in length. The coding region is 660 nucleotides (not including the initiation and termination codon) flanked by a 5'-untranslated region of 39 nucleotides and a 3'-untranslated region of 182 nucleotides. The sequence of RNA4 is present in and located at the 3'-end of RNA (Gould, A. R. and Symons, R. H. (1978) Eur. J. Biochem. 91:269–278).

The complete nucleotide sequence of AMV RNA3 has been disclosed (Barker, R. F. et (1983) Nucl. Acids Res. 11:2881–2891). A 240 nucleotide 5'-noncoding region precedes a 903 nucleotide open reading frame (ORF). This ORF is followed by a 49 nucleotide intercistronic region and a 666 nucleotide ORF, this latter ORF encoding AMV coat protein. The coat protein gene is followed by a 179 nucleotide 3'-untranslated sequence. AMV RNA4 is identical to and determined by the sequences at the 3' portion of RNA3, having 36 nucleotides of the intercistronic region, the coat protein structural gene, and the 3'-untranslated sequence.

The complete nucleotide sequence of AMV RNA1 has been obtained (Cornelissen, B. J. C. et al. (1983) Nucl. Acids Res. 11:1253–1265) RNA1 is 3645 nucleotides in length and it contains a long ORF for a protein of $M_r$ 125,685 flanked by a 5'-untranslated sequence of 99 nucleotides and a 3'-untranslated region of 163 nucleotides.

Comparison of the 3'-terminal sequences of all four AMV RNAs reveal extensive homology between the 3'-terminal 140 to 150 nucleotides (Houwing, C. J. and Jaspers, E. M. J. (1978) Biochem. 17:2927–2933). There are about 20 base substitutions in the 3'-terminal 145 nucleotides of the AMV RNAs; these are either located in the loops of base-paired structures or convert A-U base pairs to G-C base pairs in the stems of the secondary structure hairpins (Koper-Zwarthoff, E. C. et al. (1979) Nucl. Acids Res. 7:1887-1900).

AMV RNA1 and RNA2 code for two proteins, P1 and P2 respectively. These proteins are thought to be involved in the replication of the viral RNAs in plants (Nassuth et al. (1981) J. Gen. Virol. 53:207-214; Nassuth and Bol (1983) Virology 124:75-84). RNA3 is dicistronic and contains the genes for the 32K protein, P3, which is thought to be involved in the cell-to-cell movement of infection (Atabekov and Dorokhov (1984) Adv. Virus Res. 29:313-364), and coat protein. The coat protein is not translated from RNA3, but rather from a subgenomic molecule, RNA4. All of the AMV RNAs share homologous sequences at their 3' ends. Applicants have concluded that replication, cell-to-cell movement, and encapsidation of AMV are targets for genetic manipulation to bring about a reduction in the multiplication of th virus in plants.

Antisense RNA

Weintraub, H. al. (1985) Trends Genet. 1:22-25, reviews published and unpublished results using antisense RNA for genetic analysis. Travers, A. (1984) Nature 311:410, and Laporte, D. C. (1984) Trends Biochem. Sci. 9:463, review regulatory roles of antisense RNA (aRNA).

In nature, antisense or complementary RNA can function in a regulatory manner. In *E. coli*, a 174 nucleotide ompC RNA regulates ompF expression. Those antisense RNAs, which would most likely bind to mRNA regions that come in contact with ribosomes, seemed most effective in decreasing gene expression (Mizuno, T. et al. (1984) Proc. Natl. Acad. Sci. USA 81:1966-1970; Coleman, J. et al. (1984) Cell 37:429-436). Complementary RNA can also inhibit DNA replication (Tomizawa, J. al. (1981) Proc. Natl. Acad. Sci. USA 78:1421-1425; Tomizawa, J. and Itoh, T. (1982) Cell 31:575-583.

In vitro, an oligonucleotide complementary to as little as five nucleotides of the 3'-terminal region of *E. coli* 16S ribosomal RNA can inhibit translation initiation of bacterial virus mRNAs (Eckhardt, H. and Luhrmann, R. (1979) J. Biol Chem. 254:11185-11188; Jayaraman, K. et al. (1981) Proc. Natl. Acad. Sci. USA 78:1537-1541; Taniguchi, T. and Weissmann, C. (1978) Nature 275:770-772).

In vitro translation of mRNA can be inhibited if the mRNA is mixed with a complementary DNA (cDNA) and subjected to nucleic acid annealing conditions; an unannealed mixture of mRNA and cDNA can be translated (Paterson, B. M. et al. (1977) Proc. Natl. Acad. Sci. USA 74:4370-4374). In vitro replication of plant viral RNA fragments can be inhibited if the RNA fragments are mixed with a cDNA and subjected to annealing conditions; an unannealed mixture of the RNA fragments and cDNA can be replicated (Ahlquist, P. et al. (1984) Plant Mol. Biol. 3:37-44).

Rous sarcoma virus replication and cell transformation is inhibited by addition of an oligonucleotide complementary to 13 nucleotides of a 5' and 3' terminal repeat (Zamecnik, P. C. and Stephenson, M. L. (1978) Proc. Natl. Acad. Sci. USA 75:280-284).

Globin antisense RNA (aRNA) inhibited translation of globin mRNA when both were injected into the cytoplasm of frog oocytes. The aRNA inhibited translation when injected with or before mRNA. aRNA:mRNA hybrids appeared to form within the oocytes, though the hybrids were much shorter than expected for full-length duplexes (Melton, D. A. (1985) Proc. Natl. Acad. Sci. USA 82:144-148). Results suggest that secondary structure could limit the regions of nucleic acids which formed hybrids.

Production of viral antisense RNA sequences has been shown to partially protect *E. coli* against infection by the corresponding bacteriophage. Sequences complementary to ribosome binding sites were more effective inhibitors than a sequence complementary to the 3'-end of a structural gene or the 3'-untranslated region (Coleman. J. et al. (1985) Nature 315:601-603).

Antisense RNA can reduce gene expression in transient expression systems in mouse cells. When a herpes simplex virus (HSV) thymidine kinase (TK) gene and a 100-fold excess of a modification of that gene, having the protein-encoding sequence flipped so that a TK aRNA was encoded, were coinjected into TK⁻ cells, TK activity was observed to drop 4-fold (Izant, J. G. and Weintraub, H. (1984) Cell 36:1007-1015) relative to the activity observed in TK⁻ cells receiving only the TK gene.

Lac gene expression in mouse cells was observed to be reduced 10-fold when cotransformed with a lac aRNA gene at a 1:1 or higher gene:aRNA gene ratio (Rubenstein, J. L. R. et al. (1984) C. R. Acad. Sci., Paris 299:271-274).

SUMMARY OF THE INVENTION

Figure 1:
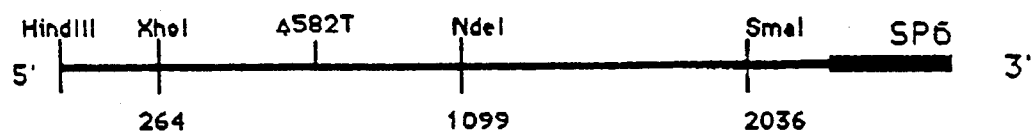
FIG. 1 shows the pGEMA3L construct of this invention. The cDNA of AMV RNA3 was cloned into the HindIII/SmaI site of pGEM2 (Progmega Biotec). There is a single T deletion at position 582. The pGEMA3M and pGEMA3S plasmids were derived from pGEMA3L by deletion of either the NdeI/SmaI fragment or the XhoI/SmaI fragment respectively. The open reading frame for P3 extends from position 241 to 1143. The gene encoding coat protein includes nucleotides 1193 to 1856. Sp6 polymerase was used to transcribe the antisense RNAs.

This invention relates to the occurrence of viral infections in plants and to the efforts of horticulturists and agronomists to combat these infections in economically significant plant species. Virus infections occur in every known plant species and cause significant reductions in the yield and quality of all agricultural and horticultural plant species. The plant industry in no country in the world is exempt from such virally caused damage and no consistent treatment is known to treat or prevent such viral infections. For example, 90% of the cassava plants in Kenya are infected by cassava mosaic virus resulting in an estimated 75% reduction in yield. As another example, in a recent viral epidemic in Ghana, more than one hundred million cacao trees were lost by infection with swollen shoot virus. Many other examples could be given making it evident that viral epidemics and infections have a vast economic significance. The reduction in yield from food crops is also relevant to the steadily increasing human population of the world and to the chronic malnutrition that already exists. Therefore, it is clear that both the means for creating virus-resistant plant genotypes and the resultant plants themselves would be very useful for increasing the world's ability to feed itself.

In particular, alfalfa mosaic virus has been shown to cause serious decreases in crop yield. AMV infects alfalfa and other annual legume crops. This is economically important; in the United States alone approximately 30 million acres are planted in alfalfa. Alfalfa mosaic virus also causes economically important diseases in crop plants such as peppers, potatoes, celery, peas, and beans. Alfalfa can be an overwintering host from which aphids carry the virus. The disease is also spread from alfalfa to other species of crop plants following a build-up of aphid infestation. In many cases, plants infected by AMV show no symptoms, making it difficult to detect the occurrence and spread of the disease. In other cases, the mosaic disease is evident but by that time the virus has almost certainly spread through a large area of plants in a field.

Apart from the removal of infected plants, there are no practical methods developed for preventing the spread of AMV. Therefore, it is clear that both the means for creating AMV-resistant genotypes and the resulting plants would be very useful for increasing agricultural productivity of a number of crops.

Therefore, it is an object of the present invention to provide plants having novel virus resistance genes, in particular, to provide plants resistant to AMV infection. Toward this goal, methods for creating viral resistance genes, in particular, antisense RNA to AMV RNA3, both complete and partial, and both including and not including coat protein or aRNA4, genes inhibitory to viral function, are provided. Also provided are plants, plant cells, plant tissues, and plant seeds containing aRNA genes which are responsible for those plant materials having an AMV resistance phenotype. Furthermore, DNA molecules useful for creating such virus resistant plants are also described. The present invention is exemplified by putting an aRNA gene complementary to alfalfa mosaic virus RNA3 and/or coat protein messenger RNA into tobacco.

Antisense RNA has never been shown to affect gene expression in plants, though it has been shown to do so in some nonplant systems. There are a number of reasons why the presence of viral aRNA might not protect a plant from a viral infection. Viral aRNA is an RNA that is not naturally found in the nucleus; viral aRNA might not be stable in that environment The level of accumulation of aRNA might be too low to inhibit infection. The aRNA may not accumulate in a part of a cell where viral infections are initiated or maintained. Though viral aRNA can be stable in plant cytoplasm, viral aRNA might not be stable in a plant cytoplasm in the absence of a viral infection. A viral infection might become established faster than aRNA could anneal to viral RNA. Accumulation of viral aRNA molecules at levels sufficient to interfere with a virus's life-cycle might be toxic to plant cells.

The mechanisms by which aRNA protects against viral infection are not known. It is believed that the presence of coat protein is necessary for infection by AMV.

The present invention exemplified using AMV shows that aRNA to AMV RNA4 (coat protein) is effective in inhibiting infection, and that aRNA to sections of AMV RNA3 not containing coat protein are effective. Moreover, aRNA to complete RNA3 containing aRNA to coat protein RNA are significantly more effective than aRNA to RNA3 alone.

DETAILED DESCRIPTION OF THE INVENTION

The following definitions are provided in order to remove ambiguities as to the intent or scope of their usage in the specification and claims.

Promoter: Refers to sequences at the 5'-end of a structural gene involved in initiation of transcription. A plant-expressible promoter is any promoter capable of driving transcription in at least one type of plant cell in at least one developmental stage. Eukaryotic promoter sequences are commonly recognized by the presence of DNA sequences homologous to the canonical form 5' . . . TATAA . . .3' about 10–30 base pairs (bp) 5' to the location of the 5'-end of the mRNA (cap site). About 30 bp 5' to the TATAA, another promoter sequence is often found which is recognized by the presence of DNA sequences homologous to the canonical form 5' . . . CCAAT . . .3'.

Transcript Terminator: Refers herein to any nucleic acid sequence capable of determining the position of the 3'-end of a transcript. The transcript terminator DNA segment may itself be a composite of segments derived from a plurality of sources, naturally occurring or synthetic, prokaryotic, or eukaryotic, and may be from genomic DNA or an mRNA-derived cDNA (mRNA: messenger RNA). Transcript termination sites include polyadenylation sites and sites determining the 3'-end of ribosomal RNAs (rRNAs), transfer RNAs (tRNAs), and nonpolyadenylated mRNAs (e.g., histone mRNA: Krieg, P. A. and Melton, D. A. (1984) Nature 308:203–206).

A polyadenylation site is a nucleic acid sequence correlated with polyadenylation of mRNA in eukaryotes, i.e., after transcriptional termination polyadenylic acid "tails" are added to the 3'-end of mRNA precursors. Polyadenylation sites are commonly recognized by the presence of homology to the canonical form 5' . . . AATAAA . . .3', although variations of distance 5' to the 3'-end of the transcript, partial "read-thru", and multiple tandem canonical sequences are not uncommon. DNA sequences between 20 to 35 bp downstream from the transcript's 3'-end seem to be necessary (McDevitt, M. A. et al. (1984) Cell 37:993–999). It should be recognized that a canonical "polyadenylation site" may actually determine the location of the 3'-end of the mRNA and not polyadenylation per se (Proudfoot, N. (1984) Nature 307:412–413; Birnstiel, M. L. et al. (1985) Cell 41:349–359).

Transcription Controlling Sequences: Refers to a promoter/transcript terminator site combination flanking a structural gene. The promoter and terminator DNA sequences flanking a particular foreign structural gene need not be derived from the same source genes (e.g., pairing two different T-DNA transcripts) or the same taxonomic source (e.g., pairing sequences from T-DNA with sequences from non-T-DNA sources such as plants, animals, fungi, yeasts, eukaryotic viruses, bacteria, and synthetic sequences).

Antisense RNA (aRNA): Refers herein to an RNA that is in part or in whole complementary to at least one viral mRNA (sense) sequence. A target virus is a virus to which one wants resistance The target viral sequence comprised in complement by the aRNA may consist of a full-length target viral mRNA or a portion thereof, the portion being from a coding region, a translation initiation site and/or a 5', 3', or internal untranslated region. An aRNA may include sequences complementary to a plurality of distinct viruses, thereby conferring resistance to each of the plurality of viruses. The aRNA itself may or may not function as an mRNA.

Antisense RNA Gene (aRNA gene): Refers herein to a promoter, a DNA sequence determining an aRNA, and a transcript terminator; the promoter, the aRNA, and the terminator having such position and orientation with respect to each other that, when in a plant cell, an aRNA may be transcribed under control of the promoter. In other words, an aRNA gene expresses an RNA comprising an RNA complementary to a viral mRNA. An aRNA gene may be a composite of segments derived from a plurality of sources, naturally occurring or synthetic. An aRNA gene from a transcript may include sequences derived in whole or in part from prokaryotic DNA, eukaryotic DNA, episomal DNA, plasmid DNA, genomic DNA, cDNA, viral DNA, viral cDNA, chemically synthesized DNA, or the like. It is further contemplated that an aRNA gene may contain one or more modifications in either the transcription control sequences, transcribed sequences, or viral cDNA, which could affect the biological activity or chemical structure of the aRNA, the rate of expression, or the manner of expression control. Such modifications include, but are not limited to, mutations, insertions, deletions, and substitutions of one or more nucleotides, and modifications that do not alter aRNA function but which affect intercellular localization, transport, or stability of the aRNA. DNA encoding an aRNA may determine an uninterrupted aRNA sequence or it may include one or more introns, bounded by the appropriate plant-functional splice junctions, which may be obtained from a synthetic or a naturally occurring source.

cDNA (Complementary DNA): Though this term is well understood in the art, it has two meanings. (1) A cDNA can be a single-stranded DNA complementary to an RNA (e.g., a viral mRNA). (2) A cDNA can also be a double-stranded DNA segment, one strand of which is complementary to an RNA, the other strand having a sequence equivalent to that RNA (substituting T for U). Generally, a double-stranded cDNA is derived from a single-stranded cDNA. However, as defined herein, a double-stranded DNA encoding mRNA sequences, e.g., the DNA of a structural gene, is included within the term cDNA. Within the Claims, cDNA always refers to the double-stranded form (meaning (2)). Elsewhere in this specification, the meaning of cDNA is defined by context and will be well understood by those in the art.

Plus-Stranded: Refers to RNA viruses whose genomes encode the virus' messenger RNA (mRNA). AMV is an example of a plus-stranded virus; each of the four RNAs found in AMV virions is capable of serving as an mRNA.

Tripartite RNA Genome: Refers to organization of a virus' genetic material. "Genome" refers to the total genetic material of the virus. "RNA genome" states that as present in virions (virus particles), the genome is in RNA form. "Tripartite" indicates that the genome is divided among three separate RNA molecules. An example of a virus with a tripartite RNA genome is AMV. The genome of AMV is carried by AMV RNAs 1, 2, and 3. Sequence of RNA4 is totally contained within RNA3, and RNA4 is not replicated; therefore, RNA4 is referred to as a subgenomic RNA and is not counted as one of the genomic RNAs.

Translation Initiation Site: Refers herein to the 5'AUG3' translational start codon at the 5'-end of a structural gene, the nucleotide following the AUG, and the 3 nucleotides preceding the AUG (see Kozak, M. (1983) Microbiol. Rev. 47:1–45; and Kozak, M. (1984) Nucl. Acids Res. 12:857–872).

5'-Untranslated Sequence: Refers herein to the part of an mRNA between its 5'-end, or "cap site", and the translational start codon.

3'-Conserved Sequence: Refers herein to a sequence at the 3'-end of a multipartite, nonpolyadenylated RNA genome that is the same for all genome components. The AMV 3'-conserved sequence extends about 145 nucleotides from the 3'-end of all 4 AMV RNAs.

Essentially Full-Length cDNA: Refers herein to a cDNA that is complementary to an entire mRNA, possibly excepting a few (e.g., five) nucleotides at either end of that mRNA sequence.

Plant-Expressible Selectable or Screenable Marker: Refers herein to a genetic marker functional in a plant cell. A selectable marker (e.g., a kanamycin resistance gene) allows cells containing and expressing that marker to grow under conditions unfavorable to growth of cells not expressing that marker. A screenable marker (e.g., a betagalactosidase gene) facilities identification of cells which express that marker.

Transforming: Refers to the act of causing a cell to contain a nucleic acid molecule or sequence not originally part of that cell.

Plant Tissues: Includes differentiated and undifferentiated tissues of plants including but not limited to roots, shoots, pollen, seeds, tumor tissue, such as crown galls, and various forms of aggregations of plant cells in culture, such as embryos and calluses. The plant tissue may be in planta or organ, tissue, or cell culture.

Plant Cell: As used herein includes plant cells in planta and plant cells and protoplasts in culture.

The following terms are well-known in the art and are not specifically defined herein: single-stranded, genome, alfalfa mosaic group (see Matthews, R. E. F. (1982) Classification and Nomenclature of Viruses, p 177), Tobamovirus (see Matthews supra, pp 158–159), CaMV 19S promoter (see Hohn, T. et al. (1982) Curr. Top. Microbiol. Immunol. 96:193–236), octopine-type T-DNA (positions, orientations, and open reading frames (ORFs) are defined as designated by Barker, R. F. et al. (1983) Plant Mol. Biol. 2:335–350), T-DNA border repeat, transcription under control of a promoter, ligating, descended, and structural gene.

Production of a genetically modified cell expressing an aRNA gene combines the specific teachings of the present disclosure with a variety of techniques and expedients known in the art. In most instances, alternative expedients exist for each stage of the overall process. The choice of expedients depends on variables such as the choice of the particular virus to which resistance is desired, the basic vector system for the introduction and stable maintenance of the aRNA gene, the plant species to be modified, the desired regeneration strategy, the particular transcriptional control sequences used, the particular viral sequences comprised by the aRNA gene transcript, and the like, all of which present alternative process steps which those of ordinary skill are able to select and use to achieve a desired result. As novel means are developed for the stable insertion and transcription of foreign DNA in plant cells, those of ordinary skill in the art will be able to select among those alternate process steps to achieve a desired result. The fundamental aspects of the invention are the nature of the aRNA gene and its use to confer resistance to viral infections of plants transformed therewith. Other aspects include the nature and structure of the aRNA sequence and its means of insertion and expression in a plant genome. The remaining steps of the preferred embodiment for obtaining a genetically modified plant include inserting the aRNA gene into T-DNA, transferring the modified T-DNA to a plant cell wherein T-DNA becomes stably integrated as part of the plant cell genome, techniques for in vitro culture and eventual regeneration into whole plants, which may include steps for selecting and detecting transformed plant cells and steps of transferring the introduced aRNA gene, and other linked or cotransformed DNA sequences from the originally transformed strain into commercially acceptable cultivars, and monitoring expression in transformed plants.

A starting point for construction of an aRNA gene is obtaining DNA clones of viral sequences. If the virus is a DNA virus, the DNA clones are obtainable using methods well-known in the art of recombinant DNA. If the virus is an RNA virus, a cDNA clone must be made from the viral sequence desired. A number of methods for making cDNA clones are known in the art of recombinant DNA; choice of methods will depend on variables such as polyadenylation, RNA length, prior knowledge of RNA sequence, prior preparations within the particular laboratory for other cDNA cloning experiments, and the like. Cloned viral sequences are a necessary component of an aRNA gene.

A principal feature of the present invention in its preferred embodiment is the construction of a T-DNA derivative having an inserted gene under control of plant-expressible transcription controlling sequences, i.e., between a promoter and a transcript terminator, as these terms have been defined, supra. The aRNA-encoding DNA must be inserted in correct position and orientation with respect to the promoter. Position relates to on which side of the promoter the aRNA-encoding DNA is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of an aRNA-encoding DNA insertion must be "downstream" from the promoter. Orientation refers to the directionality of the structural gene. That portion of an aRNA-encoding DNA which is complementary to viral mRNA encoding the amino terminus of a viral protein is termed the 3'-end of the aRNA-encoding DNA, while that end which is complementary to viral mRNA encoding amino acids near the carboxyl end of the protein is termed the 5'-end of the aRNA-encoding DNA. In other words, the 5'-end and the 3'-end of the aRNA-encoding DNA respectively encode the 3'-end and the 5'-end of viral mRNA. Correct orientation of the aRNA-encoding DNA is with the 5'-end thereof proximal to the promoter. Similarly to the promoter region, the transcript terminator must be located in correct position and orientation relative to the aRNA, being proximal to the 3'-end of the aRNA. Differences in levels of aRNA gene expression or in developmentally-regulated expression may be observed as a function of aRNA components, promoters, transcript terminators, flanking DNA sequences, or sites of insertion into the transformed plant's genome. aRNA accumulation may also be greatly influenced by the details of the aRNA secondary structure, especially stem-loop structures. Different properties, including, but not limited to, such properties as stability, intracellular localization, post-transcriptional processing, and other functional properties of the expressed aRNA itself may be altered when aRNA gene components are varied. All of these variations present numerous opportunities to manipulate and control the ultimate expression of the viral resistance phenotype, depending upon the desired result within the plant cell, plant tissue, and whole plant.

The fundamental principle of the present invention is that the presence of an antisense RNA sequence in a plant cell is capable of conferring at least some level of viral resistance to that cell. The requirements for which viral sequence are to be included in an aRNA are best couched in functional terms. The presence of aRNA in a cell confers viral resistance by interfering with one or more viral functions. Such functions might include translation of viral proteins, replication of viral RNAs, encapsidation of viral nucleic acid, etc. aRNA presumably interferes by annealing to the complementary viral segment, followed by degradation of the double-stranded molecule. Alternatively, the annealing process may prevent binding of at least one protein to the viral RNA that is required for completion of the viral lifecycle. There are four important regions within a full-length viral sequence, to which an aRNA can anneal: a 5'-untranslated sequence, a translational initiation site, a structural gene, and a 3'-conserved sequence. Binding of an aRNA to a 5'-untranslated sequence may interfere with translational initiation by interfering with preinitiation scanning of the mRNA for translational initiation sites by 40S ribosomal subunits (see Kozak, M. (1983) Microbiol. Rev. 47:1-45). Binding to a translational initiation site may interfere with translational initiation. Binding to the structural gene sequence, i.e., the protein-encoding sequence, may lower translational efficiency. Binding to the 3'-conserved sequence may interfere with initiation of replication.

The present invention is not limited by the mode or mechanism of interference. The aRNA need not comprise a full-length viral sequence; any sequence segment complementary to a viral plus-strand segment and capable of interfering with a viral function is sufficient. In other words, the presence of at least one sequence capable of interfering with viral functions is required in an aRNA and any sequence segment incapable of such interference may be dispensed with, subject to considerations of RNA stability, cellular localization, and the like. Antisense sequences derived from several distinct viruses, each such sequence being capable of functioning separately as an aRNA, may be combined to form an aRNA having antiviral activity against each of the several viruses.

As defined, an aRNA may include nonviral sequences. Even in cases where the aRNA is derived from a full-length viral sequence it may also include nonviral sequences. Usually these nonviral sequences will be at the 5'- and 3'-ends of the aRNA. Often these nonviral components will be derived from promoter or transcript terminator DNA segments. Inclusion of various nonviral sequences may affect RNA stability, level of expression, cellular localization of aRNA, post-transcriptional processing, and the like. It is known to the art that RNA stability is affected by terminal structures such as 5'-capping and 3'-polyadenylation and by the extent of internal structure, i.e., intramolecular base-pairing. The level of expression is determined by the promoter element itself as well as enhancer elements that may be located upstream or downstream of the promoter or even within the gene itself. An aRNA may be stabilized by binding to certain proteins within the cell. This may be accomplished by including sequences in the aRNA that promote such protein binding. An intron may be included in an aRNA, provided that, if the splice sites are derived from two different genes, the intron splice sites be compatible.

An aRNA useful for controlling viral disease must be designed with several biological factors in mind. RNA secondary structure may affect antiviral activity as well as stability and processing. In particular, intramolecular base-pairing involving sequences which interfere with viral functions must not be so strong that annealing to viral mRNA is precluded. An aRNA transcript should be incapable of being converted by the viral replication machinery into a functional sense viral component capable of increasing the severity of the viral disease. Production of sense-strand may be blocked by inclusion in the aRNA of nonviral sequences, especially at one or both aRNA ends, which interfere with replicase function. Should plus-strand production not be blocked, other steps may be taken. The deletion of a protein-encoding sequence segment of the aRNA or introduction of an appropriately positioned frameshift mutation in the aRNA can cause the viral protein templated by the sense-strand derived from the aRNA to be nonfunctional. Frameshift mutations are conveniently introduced by opening a viral cDNA-carrying plasmid at a unique, sticky-end generating restriction site, removing the sticky-ends, and religation. Depending on the enzyme and methods used this will delete or insert two or four base-pairs, thereby generating a frameshift (and also eliminating that restriction site).

Combining of DNA segments, including viral, nonviral, promoter, and transcription terminator sequences, to form an aRNA gene is accomplished by means known and understood by those of ordinary skill in the art of recombinant DNA technology. Choice of promoter depends on the developmental regulation desired. Use of developmentally regulated promoters for gene expression in plants is described in the Background. T-DNA or CaMV promoters are advantageous since they are generally considered constitutive. The RuBP-Case small subunit promoter may be useful for expression in the green tissues of an aRNA gene-transformed plant. In the preferred embodiments, the transcript terminator is a polyadenylation site. The plant gene source of the polyadenylation site is not crucial provided that the polyadenylation site, the promoter and the aRNA are compatible for transcription and post-transcriptional processing.

As will be apparent to those of ordinary skill in the art, the aRNA gene combination may be placed between any restriction sites convenient for removing the combination from the plasmid it is carried on and convenient for insertion into the plant transformation vector of choice. For example, location of the aRNA gene insertion within T-DNA is not critical as long as the transfer function of sequences immediately surrounding the T-DNA borders is not disrupted, since in prior art studies these regions appear to be essential for insertion of the modified T-DNA into the plant genome. The combination is inserted into the plant transformation vector by standard techniques well-known to those skilled in the art. The orientation of the assembled aRNA gene, with respect to the direction of transcription and translation of endogenous vector genes is not usually critical; generally, either of the two possible orientations is functional.

As reviewed in the Background (Ti Plasmid DNA), T-DNA of micro-Ti plasmids can be transferred from an Agrobacterium strain to a plant cell provided the Agrobacterium strain contains certain trans-acting genes whose function is to promote the transfer of T-DNA to a plant cell. Micro-Ti plasmids are advantageous in that they are small and relatively easy to manipulate directly, eliminating the need to transfer the gene to T-DNA from a shuttle vector by homologous recombination. After the desired aRNA gene has been inserted, they can easily be introduced directly into an Agrobacterium cell containing trans-acting vir genes, the vir genes usually being on a "helper plasmid" that promotes T-DNA transfer. Introduction into an Agrobacterium strain is conveniently accomplished either by transformation of the Agrobacterium strain or by conjugal transfer from a donor bacterial cell, the techniques for which are well-known to those of ordinary skill. For purposes of introduction of novel DNA sequences into a plant genome, Ti plasmids, Ri plasmids, micro-Ti plasmids, and T-DNA integrated into chromosomes should be considered functionally equivalent.

T-DNA having an aRNA gene can be transferred to plant cells by any technique in the art. For example, this transfer is most conveniently accomplished by cocultivation of the Agrobacterium strain with plant cells or with plant tissues. Using these methods, a certain proportion of the plant cells are transformed, that is to say have T-DNA transferred therein and inserted into the plant cell genome. In either case, the transformed cells must be selected or screened to distinguish them from untransformed cells. Selection is most readily accomplished by providing a selectable marker gene that is incorporated into the T-DNA in addition to the aRNA gene. Examples of artificial markers include those reviewed in the Background (see the sections on Chimeric Genes). In addition, the T-DNA itself can provide selectable markers such as the gene(s) controlling abnormal morphology characteristics of Ri-induced tumor roots and the gene(s) that control resistance to toxic compounds such as amino acid analogs, this resistance being provided by the opine synthesizing enzyme (encoded by the ocs gene). Screening methods well-known to those skilled in the art include, but are not limited to, assays for opine production, specific hybridization to characteristic nucleic acid sequences (e.g., aRNA or T-DNA) or immunological assays for specific proteins (e.g., kanamycin resistance gene). Additionally, a phenotype of an expressed aRNA gene (e.g., resistance to a target virus) can be used to identify transformed tissue. Assay of viral resistance may be done by one of a number of methods well-known in the art of plant virology, including detection of decreased production of a virus component (e.g., a viral RNA or a viral protein), decreased infectivity as assayed by protoplast infection or local lesion assays, decreased production of progeny virus, and the like.

Although the preferred embodiments involve use of micro-Ti plasmids, other T-DNA-based vector systems known to the art may readily be substituted. Futhermore, though the preferred embodiment of this invention incorporates a T-DNA-based Agrobacterium-mediated system for incorporation of the aRNA gene into the genome of the plant which is to be transformed, other means for transferring and incorporating the aRNA gene are also included within the scope of this invention. Other means for the stable incorporation of the aRNA gene into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, fusion with vector-containing liposomes or bacterial spheroplasts, microinjection, encapsidation in viral coat protein followed by an infection-like process, direct uptake of DNA, possibly after induction of plasmalemma permeability by an electric pulse, a laser, or a chemical agent, and bombardment with DNA-coated microprojectiles. Means for transient incorporation and/or expression are also included within the scope of this invention. Systems based on Agrobacterium cells and T-DNAs can be used to transform angiosperms, including dicots and monocots, by transfer of DNA from a bacterium to a plant cell; systems based on alternate vectors or means for vector delivery may be used to transform gymnosperms and angiosperms.

Regeneration of transformed cells and tissues is accomplished by resort to known techniques. An object of the regeneration step is to obtain a whole plant that grows and reproduces normally but which retains the desired introduced DNA in an integrated form. The techniques of regeneration vary somewhat according to principles known in the art, and may depend upon the plant transformation vector and the species of the transformed plant. Regeneration of transformed tissues of tobacco, petunia, tomato as well as several other species including a number of monocots is well-known to the art. As means for regeneration of additional plant species are developed, the art will understand, without undue experimentation, how to adapt these newly discovered means for regeneration to transformed plant tissues.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced aRNA gene may be readily transformed to the desired agronomic cultivar by techniques well-known to those skilled in the arts of plant breeding and plant genetics. Sexual crosses of transformed plants with the agronomic cultivars yield initial hybrids. These hybrids can then be back-crossed with plants of the desired genetic background. Progeny are continuously screened and/or selected for the continued presence of integrated aRNA gene DNA, T-DNA, or for a new phenotype resulting from expression of the aRNA gene or other genes carried by the inserted DNA. In this manner, after a number of rounds of back-crossing and selection, plants can be produced having a genotype essentially identical to the agronomically desired parents except for the addition of desirable, introduced DNA sequences.

An alternative to stable incorporation of an aRNA gene into a plant genome for making an aRNA-containing plant cell is to infect a plant with a vector viral RNA capable of being maintained in that plant, the viral RNA having aRNA sequences to a distinct target virus (i.e., a virus from which one wants protection). Typically, double-stranded cDNA sequences of the vector virus and the target virus are manipulated using recombinant DNA technology. After assembly of a DNA sequence corresponding to that of the desired vector RNA/target aRNA combination, the plant viral vector cDNA/aRNA cDNA combination may be placed behind a promoter that can drive in vitro transcription. Descriptions of such vectors and conditions for their use include Melton, D. A. et al. (1984) Nucl. Acids Res. 12:7035–7056; Krieg, P. A. and Melton, D. A. (1984) Nucl. Acids Res. 12:7057–7070, Ahlquist, P. and Janda, M. (1984) Mol. Cell. Biol. 4:2876–2882, and French, R. et al. (1986) Science 231:1294–1297. After such a viral vector/aRNA/in vitro transcription vector combination is assembled, a viral vector RNA/target aRNA combination may be produced by in vitro transcription and mixed with any other viral RNA components necessary for maintenance of the viral vector in a plant cell. Infection of a plant cell by a vector/aRNA combination may then be effected by known methods and, after inoculation with the target virus or target virus RNA, inhibition of infection or decreased production of a viral component may be assayed by methods well-known in the art.

Similarly, plant viral DNA vectors may be used to introduce an aRNA gene into a plant cell. The utility of such vectors has been demonstrated by Brisson, N. et al. (1984) Nature 310:511–514. The means for creating functional aRNA genes as taught by the present invention can be combined with use of plant DNA virus-based vectors by those of ordinary skill in the art. After infection of an appropriate plant host cell, inhibition of target virus infection may be assayed as described above.

The Examples describe the use of aRNA to AMV coat protein and/or of AMV RNA3 in reducing AMV infection. Antisense AMV RNAs can reduce the expression of AMV in whole plants, when their cDNAs are transformed into plants, preferably alfalfa or tobacco so as to produce sufficient quantities of antisense RNA. The antisense RNA from full-length AMV RNA3 pGEMA3L is preferred for reducing expression of AMV in plants in light of the following experimental findings as shown in the examples i) antisense RNA from full-length RNA3 was able to reduce the level of P3 and coat protein production in in vitro translation experiments. In whole plants, the production of this antisense RNA would reduce or shut down the production of both P3 and coat protein. Coat protein production is required for the production of mature virions, and P3 is probably required for the movement and spread of the virions through plant tissue. Infection by AMV in these transformed plants would be reduced or halted, since both P3 and AMV coat protein are required for infection by AMV; and ii) this particular antisense RNA was the most successful at reducing the percentage of infected protoplasts and the detection of P3 when coinoculated with AMV RNA or AMV virions. The preference for use of the antisense RNA from full-length RNA3 may be due to the fact that this antisense RNA has the potential to operate directly on several different stages of AMV infection. In addition to the direct inhibition of RNA3 and RNA4 translation described in (i), the possibility exists that this antisense RNA, which is complementary to the conserved 3' ends of the AMV RNAs, would cause reduced or altered replication.

EXAMPLES

The following Examples are presented for the purpose of illustrating specific embodiments within the scope of the present invention without limiting the scope, the scope being defined by the Claims. Numerous variations will be readily apparent to those of ordinary skill in the art.

The Examples utilize many techniques well-known and accessible to those skilled in the arts of molecular biology and manipulation of T-DNA and Agrobacterium: such methods are fully described in one or more of the cited references if not described in detail herein. All references cited in this specification are hereby incorporated by reference. Enzymes are obtained from commercial sources and are used according to the vendors' recommendations and other variations known to the art. Reagents, buffers, and cultures are also known in the art. Reference works containing such techniques include the following: Wu, R. (ed.) (1979) Methods Enzymol. 68; Wu, R. et al. (eds.) (1983) Methods Enzymol. 100 and 101; Grossman, L. and Moldave, K. (eds.) (1980) Methods Enzymol. 65; Weissbach, A. and Weissbach, H. (eds.) (1986) Methods Enzymol. 118 (see especially Rogers, S. G. et al. pp 627-640); Miller, J. H. (1972) *Experiments in Molecular Genetics*: Davis, R. et al. (1980) *Advanced Bacterial Genetics*; Schleif, R. F. and Wensink, P. C. (1982) *Practical Methods in Molecular Biology*; Walker, J. M. and Gaastra, W. (eds.) (1983) *Techniques in Molecular Biology*; and Maniatis, T. et al. (1982) *Molecular Cloning*. Additionally, Lathe, R. F. et al. (1983) Genet. Eng. 4:1–56, make useful comments on DNA manipulations.

Textual use of the name of a restriction endonuclease in isolation, e.g., "BclI," refers to use of that enzyme in an enzymatic digestion, except in a diagram where it can refer to the site of a sequence susceptible to action of that enzyme, e.g., a restriction site. In the text, restriction sites are indicated by the additional use of the word "site," e.g., "BclI site." The additional use of the word "fragment," e.g., "BclI fragment," indicates a linear double-stranded DNA molecule having ends generated by action of the named enzyme (e.g., a restriction fragment). A phrase such as "BclI/SmaI fragment" indicates that the restriction fragment was generated by the action of two different enzymes, here BclI and SmaI, the two ends resulting from the action of different enzymes.

Plasmids, and only plasmids, are prefaced with a "p," e.g., pTi15955 or pH400, and strain designations parenthetically indicate a plasmid harbored within, e.g., *A. tumefaciens* (pTi15955) or *E. coli* H802 (pH400). The following strains are on deposit.

| | |
|---|---|
| *E. coli* MC1061 (pH400A4I) | NRRL B-18062 |
| *E. coli* K802 (pH4-1) | NRRL B-18009 |
| *A. tumefaciens* (pTi15955) | ATCC 15955 |
| *E. coli* CSH52 (pSUP106) | NRRL B-15486 |
| *E. coli* SM10 | NRRL B-15481 |
| *E. coli* S17-1 | NRRL B-15483 |

(ATCC: American Type Culture Collection, 12301 Parklawn Dr., Rockville, Md. 20852 USA; NRRL: ARS Patent Collection, Northern Regional Research Center, 1815 N. University St., Peoria, Ill. 61614 USA.) Other plasmids and strains are widely available and accessible to those in the art.

EXAMPLE 1

Preparation of AMV RNA4 cDNA pSP65A4 (Loesch-Fries, L. S. et al. (1985) Virol. 146:177–187) carries a full-length cDNA copy of AMV RNA4. pSP65A4 DNA digested with EcoRI and SmaI was subjected to agarose gel electrophoresis and a 0.89 kbp fragment was eluted from the gel. This fragment was mixed with and ligated to the linear pSP64 DNA and transformed into MC1061. Ampicillin-resistant transformants were screened by hybridization to an AMV RNA4 probe. A colony was identified which harbored a plasmid, designated pSP64A4I, carrying a full-length AMV RNA4 cDNA.

pSP64 and pSP65 are designed for in vitro transcription under control of a bacteriophage SP6 promoter (Melton, D. A. et al. (1984) Nucl. Acids Res. 12:7035–7056; Krieg, P. A. and Melton, D. A. (1984) Nucl. Acids Res. 12:7057–7070). pSP65A4 and pSP64A4I respectively direct synthesis of AMV RNA4 plus-stranded sequences and AMV RNA4 aRNA sequences. When the two plasmids are cut respectively by SmaI and EcoRI, in vitro run-off transcripts are essentially full-length coat protein mRNA sequence and the complement thereto. AMV cDNA EcoRI/SmaI fragments of pSP65A4 and pSP64A4I are identical.

EXAMPLE 2

In vitro tests of coat protein aRNA inhibition of AMV infection

Alfalfa and tobacco protoplasts were infected in vitro with RNAs essentially as described by Samac, D. A. et al. (1983) Virol. 131:455–462; the major modification being that RNA was added in a small volume (e.g., 10 μl) to the protoplast pellet, which was then resuspended in residual supernatant before addition of polyethylene glycol (PEG). This modification to Samac et al.'s method of adding RNA to the PEG before combination with the protoplasts led to an approximately fifty-fold reduction in the amount of RNA needed for an infection. Conditions of inoculation do not promote formation of sense-strand:antisense-strand duplexes outside of a cell.

Synthetic RNAs were made essentially as described by Melton et al. supra and by protocol of the SP6 polymerase vendor. 5'-capped RNAs were synthesized by inclusion of 0.5 mM $^7$ mG$^{5'}$ppp$^{5'}$G and reduction of GTP concentration from 0.5 mM to 0.025 mM. Synthetic AMV RNA4 was templated by SmaI-linearized pSP64A4 and synthetic AMV RNA4 aRNA was templated by EcoRI-linearized pSP64A4I.

In a typical experiment using either alfalfa or tobacco protoplasts, natural AMV RNA1, RNA2, and RNA3 mixed with synthetic capped RNA4 resulted in infection of about two-thirds of the inoculated protoplasts. Inclusion of an equal amount, relative to the synthetic RNA4, of capped RNA4 aRNA led to at least a hundred-fold decrease in infection levels, and often to no detectable infection.

EXAMPLE 3

Preparation of CaMV transcription controlling sequences pDOB512, carrying cauliflower mosaic virus (CaMV) transcription controlling sequences (obtained from Dr. Ken Richards, Centre National de la Recherche Scientifique, Institute de Biologie Moleculaire et Cellulaire, 15, Rue Descartes, F-67084 Strasbourg, France) was constructed as follows: (For a review of CaMV, see Hohn, T. et al. (1982) Curr. Top. Microbiol. Immunol. 96:193–236.) A HindIII fragment carrying the CaMV 19S RNA promoter region (CaMV nucleotides 5376-5851) was inserted into pBR322 and was trimmed back to within one base pair of the 19S transcript cap site. A HindIII fragment carrying the CaMV 19S transcript terminator (CaMV nucleotides 7018-7794) to which BamHI linkers had been added was then inserted behind the 19S promoter; the resulting plasmid is designated pDOB412. pDOB412 DNA was digested with BglII and SalI, filled in by the Klenow fragment of E. coli DNA polymerase I, and religated, thereby deleting DNA, which includes BamHI and HindIII sites, between the CaMV position 7644 BglII site and the pBR322 position 650 SalI site and regenerating a BglII site. The resultant plasmid was designated pDOB512.

The sticky-ends of HindIII linearized pDOB512 were filled in by Klenow fragment (or alternatively by T4 DNA polymerase). The blunt-ended pDOB512 DNA was mixed with and ligated to commercially available BglII linkers which were then trimmed by digestion with BglII and religated. The ligation mix was transformed into E. coli K802 and an ampicillin-resistant transformant was isolated which harbored a plasmid, designated pDOB513. pDOB513 has CaMV 19S transcription controlling sequences on a BglII fragment. SmaI and BamHI sites are found between the DNA segments having the promoter and the polyadenylation site in both pDOB412, pDOB512, and pDOB513, thereby providing a convenient location for insertion of foreign DNA that is to be a template for a transcript.

EXAMPLE 4

Placement of AMV cDNA behind the CaMV promoter pSP65A4 DNA was digested with EcoRI and SmaI and the 0.89 kb AMV cDNA was purified by elution from an agarose gel after electrophoretic separation. The EcoRI sticky-end was converted to a blunt-end by incubation with the Klenow fragment of E. coli DNA polymerase I. After SmaI-linearized pDOB513 DNA was mixed with and ligated to the blunt-ended cDNA, the ligation products were transformed into MC1061. Plasmid DNAs isolated from ampicillin-resistant transformants were screened by hybridization of colony blots to an AMV RNA4 probe. A colony was identified which harbored a plasmid, designated pDOBA4I, having AMV cDNA inserted between CaMV 19S transcription controlling sequences oriented so that when transcribed, an aRNA would be synthesized; i.e., so that the EcoRI end and an internal BamHI site are distal to the promoter and proximal to the transcript terminator. A CaMV transcription controlling sequence/AMV aRNA combination may be removed from pDOBA4I on a 1.92 kbp Bgl II fragment.

EXAMPLE 5

Construction of pH400, a micro-Ti plasmid pH4-1 is a micro-Ti plasmid harbored by E. coli K802 (pH4-1), which is on deposit as NRRL B-18009. pH4-1 is disclosed by Sutton, D. W. et al., U.S. patent application Ser. No. 788,984, now abandoned, which is hereby incorporated by reference, and by Merlo, D. et al. (1985) Abstracts, 1st Int. Cong. Plant Mol. Biol., Galau, G. A. (ed.). pH4-1 contains two T-DNA fragments, a HinDdIII fragment spanning positions 602 and 2,290 (as defined by Barker, R. F. et al. (1983) Plant Mol. Biol. 2:335–350) carrying the left border of $T_L$ and promoter sequences associated with ORF1, and a SmaI/BclI fragment spanning positions 11,207 and 14,711, having a 3'-deleted tml, an intact ocs. and the right border of $T_L$. Between the position 3,390 HindIII site and the position 11,207 SmaI site (this SmaI site having been converted to a BglII site by insertion of BglII linkers) of these two fragments is a plant-expressible selectable marker. This marker has a CaMV 19S promoter, a Tn5 kanamycin resistance structural gene encoding neomycin phosphotransferase II, and two polyadenylation sites, one from CaMV and another from T-DNA ORF26, donated by a T-DNA fragment spanning HincII sites at positions 21,727 and 22,440. The kanamycin resistance gene is oriented parallel to ocs and tml and antiparallel to the ORFI promoter. The T-DNA/selectable marker combination is inserted into the HindIII site of pSUP106, an 11 kbp wide host-range plasmid capable of maintenance in both E. coli and Agrobacterium (Priefer, U. B. et al. (1985) J. Bacteriol. 163:324–330; E. coli CSH52 (pSUP106) is on deposit as NRRL B-15486). The T-DNA is oriented within pSUP106 so that the $T_L$ right border is proximal to the pSUP106 EcoRI site, which is present within the pSUP106 chloramphenicol resistance gene.

pH4-1 has two BglII sites, both of which flank the kan selectable marker. One of the BglII sites was removed as follows, thereby leaving a unique BglII site useful for insertion of extraneous DNA. pH4-1 DNA was linearized being partially digested with BglII and full-length, linear DNA was electrophoretically isolated. The BglII sticky-ends were then removed by incubation with the Klenow fragment of E. coli DNA polymerase I. The resulting blunt-ended DNA was ligated to itself and transformed into E. coli. Plasmid DNAs isolated from transformants resistant to chloramphenicol were screened by restriction analysis and a colony was identified which harbored a plasmid designated pH400. pH400 was identical to pH4-1 except for the absence of the BglII site between the kan gene and the ORF1 promoter, the unique pH400 BglII site being located between the kan gene and the ocs gene.

EXAMPLE 6

Insertion of an AMV4 aRNA gene into pH400 pDOBA4I DNA was digested with BglII and then mixed with and ligated to BglII-linearized pH400 DNA. After transformation into MC1061 and selection for chloramphenicol resistance, colonies were blotted and hybridized with an AMV RNA4 probe. A colony was identified which harbored a plasmid, designated pH400A4I, having an aRNA gene inserted into the pH400 BglII site. pH400A4I has an aRNA gene having full-length AMV RNA4 sequences.

EXAMPLE 7

Plant transformation pH400A4I was transferred into A. tumefaciens LBA4404 (Ooms, G. et al. (1981) Gene 14:33–50), a Vir gene-harboring, micro-Ti-mobilizing strain, by the triparental mating technique (Ruvkun, G. B. and Ausubel, F. M. (1981) Nature 289:85–88), which is well-known in the art, or by mating from a mobilizing strain of E. coli, e.g., SM10 (NRRL B-15481) or S17-1 (NRRL B-15483)

(Simon, R. et al. (1983) Biotechnol. 1:784–791). Tobacco leaf tissue was obtained from 4- or 5-week old Xanthi-nc plants grown axenically in Magenta boxes. Inoculation was by a modification of the method of Horsch, R .B. et al. (1985) Science 227:1229–1231. Inocula were prepared by placing two loopfuls of Agrobacterium cells in 10 ml of L-broth. After suspension by forceful pipetting with a Pasteur pipette, inocula could be used immediately. Leaves were excised and midribs were removed; cutting surfaces were wetted with L-broth to help keep the leaves wet. Leaf pieces were about 2–4 mm wide and about 7–10 mm long. Leaf pieces were dipped in the inoculum for 5–10 min, though in some experiments, leaf pieces were just dipped into the inoculum or were infiltrated with the inoculum in a vacuum flask. Pieces were then blotted dry on sterile filter paper and placed upside down on feeder plates prepared from a Xanthi suspension culture. The feeder plates had an SMPi medium (SMPi: MX− supplemented with 0.1 mg/l p-chlorophenoxyacetic acid (PCPA) and 7.5 mg/l 6-(8,8-dimethylallylamino) purine (2ip); MX−: 1.65 g/l $NH_4NO_3$, 1.9 g/l $KNO_3$, 440 mg/l $CaCl_2.2H_2O$), 370 mg/l $MgSO_4.7H_2O$, 170 mg/l $KH_2PO_4$, 0.83 mg/l KI, 6.2 mg/l $H_3BO_3$, 22.3 mg/l $MnSO_4.4H_2O$, 8.6 mg/l $ZnSO_4.7H_2O$, 0.25 mg/l $Na_2MoO_4.2H_2O$, 0.025 mg/l $CuSO_4.5H_2O$, 0.025 mg/l $CoCl_2.6H_2O$, 1 g/l inositol, 50 mg/l nicotinic acid, 50 mg/l pyroxidine.HCl, 50 mg/l thiamine.HCl, 30 g/l sucrose, pH 5.8, solidified with 8 g/l agar). Leaf pieces were removed from feeder plates after 4–6 days and placed on SMPi medium supplemented with 500 mg/l carbenicillin, 50 mg/l clocacillin, and 100–300 mg/l kanamycin (200 mg/l optimum). The resulting shoots were excised and placed on MX-medium supplemented with 100–300 mg/l kanamycin (200 mg/l optimum).

EXAMPLE 8

Expression in plants

Regenerated tobacco plants descended from cells transformed by *A. tumefaciens* LBA4404 (pH400A4I) were self-fertilized. The resulting seeds were germinated on MX-supplemented with 100–300 mg/l kanamycin (200 mg/l optimum) to select plants containing the aRNA gene-bearing T-DNA. Presence of pH400A4I T-DNA was confirmed by Southern blot analysis. Presence of aRNA was confirmed by Northern blot analysis. Untransformed control tobacco plants and aRNA gene-containing plants are challenged by being inoculated with all four AMV RNAs after abrasion of leaves with carborundum, a method well-known to the art. Under these conditions, translation of AMV RNA4 molecules present in the inoculum is necessary for establishment of an AMV infection. When compared to control plants, plants having an aRNA gene are observed to be resistant to AMV infection or to have reduced or delayed symptoms, depending on the degree of aRNA expression in tissues of a particular plant.

EXAMPLE 9

Antisense RNAs to AMV RNA3 and RNA4 inhibit in vitro translation in cell-free system and infection in tobacco The effects of three antisense alfalfa mosaic virus (AMV) RNAs on the translation of the 32K protein, P3, encoded by AMV RNA3 and of the coat protein were studied in in vitro translations and in cv. Xanthi tobacco protoplasts.

The antisense RNA transcripts from three plasmids (pGEMA3L, pGEMA3M, pGEMA3S) varied in length from the 5' end of RNA3 and included one full-length antisense RNA. Specifically, pGEMA3L is one base pair short of the full-length 2037 nucleotide AMV RNA3 and introduces a stop codon. pGEMA3M is 1099 nucleotides long, and pGEMA3S is 264 nucleotides long. Thus, transcripts from all three plasmids contain antisense RNA complementary to RNA3; only pGEMA3L produces transcripts with antisense RNA complementary to both AMV RNA3 and RNA4.

Construction of antisense RNA-generating plasmids: The plasmid pGEMA3L was constructed by insertion of the cDNA of AMV RNA3 into the SmaI/HindIII sites of pGEM2 (Promega Biotec). The plasmids pGEMA3S and pGEMA3M, which contain deletions of AMV RNA3 from the 3' end, were obtained by double digests of pGEMA3L with SmaI and either XhoI or NdeI respectively. Staggered ends were filled in using the Klenow fragment under the following conditions: DNA (50 ng/μl), 55 mM Tris pH7.6, 1 mM Spermidine, 10 mM $MgCl_2$, 800 μM dNTPs, 1 mM ATP, 0.2 mM DTT, and 3 units Klenow. The mixture was incubated for 10 min at room temperature, heated to 70° C. for 5 min. and ligated under conditions similar to the blunt-ending step above except that the DNA concentration was at 5 ng/μl and 1.3 units of ligase were used. The reaction components were incubated overnight at room temperature and then used in the transformation of competent MC1061 cells.

In vitro transcriptions were performed as outlined in the Promega Biotec Technical Bulletin. Dithiothreitol was made fresh prior to each set of transcription reactions. Concentrations of DNA and SP6 RNA polymerase were 5.0 μg and 45 units respectively in the 100 μl transcription reactions. Antisense RNA was labelled with 6.0 μl $^3$H-GTP (specific activity of 9.4 Ci/mmol, New England Nuclear). Reactions were incubated at 37° C. for 60 min. Incorporation of $^3$H-GTP was monitored according to McLeester and Hall (1977) Anal. Biochem. 79:627–630 except that the filters were first soaked in a solution consisting of 20% trichloroacetic acid (TCA, w/v, 8% $NaH_2PO_4$ (w/v) and 8% $Na_4P_2O_7$ (w/v). An equal amount (0.8 μl) of each reaction was spotted onto the filter disks, allowed to dry, and then soaked in a solution containing 5% TCA (w/v), 2% $NaH_2PO_4$ (w/v), and 2% $Na_4P_2O_7$ (w.v) for 15 min. (3 times 5 min. each). The resulting antisense RNA was purified by phenol and ether extractions, precipitated overnight in ethanol, pelleted and resuspended in sterile water. Antisense RNA samples to be used for gel electrophoresis were denatured by addition of urea to a final concentration of 6M and heated to 60° C. for 7 min. Gel electrophoresis and fluorography were carried out as described in Samac et al. (1983) Virology 131:455–462.

Each of the antisense RNAs were hybridized to AMV RNA prior to their use in the in vitro translation studies. The RNAs were combined in 1.5 ml of hybridization buffer, which contained 80% formamide (v/v), 0.4M NaCl, 40 mM PIPES pH 6.7, and 1 mM EDTA, and incubated at 85° C. for 5 min. to completely denature the RNAs. The mixture was then incubated at 45° C. for 2 hours to allow the antisense RNAs to hybridize to the AMV RNA. The RNAs were recovered by EtOH precipitation and used as templates in the in vitro translation reactions.

AMV RNA with or without antisense RNA was translated in a wheat germ cell free system (Davies and Kaesberg (1973) J. Virol. 12:1434–1441). The reaction mixture consisted of 2.5 µl amino acid mix (25 mM ATP, 2.5 mM GTP, 50 mM PEP, and 1.0 mM amino acids minus methionine), 2.5 µl HEPES-KOAc buffer (200 mM HEPES, 450 mM KOAc pH 7.6), 2.5 µl 1.0 mM Spermidine, 2.5 µl radiolabelled $^{35}$S-methionine (specific activity of 71 Ci/mmol, Amersham), 5.0 µl 40 mM MgOAc, and 7.5 µl wheat germ extract in a 25.0 µl total reaction volume. The reactions were incubated at 30° C. for 60 min. Incorporation of $^{35}$S-methionine was monitored according to McLeester and Hall (1977) supra. Samples were diluted by addition of an equal volume of SDS sample buffer consisting of 62.5 mM Tris-HCl pH 6.8, 40% sucrose, 2% SDS (w/v), 2 mM EDTA, 1% β-mercaptoethanol (w/v), 0.02% bromphenol blue (w/v) and boiled for 3 min. prior to electrophoresis. The buffers and polyacrylamide gels were similar to those described by Laemmli (1970) Nature (London) 227:680–685, except that the acrylamide:bisacrylamide ratio was 200:1. The separation gel was 16% acrylamide (w/v), 0.35M Tris-HCl pH 8.8, 0.1% SDS (w/v), 2 mM EDTA, 0.13% TEMED (v/v), and 0.075% ammonium persulfate (w/v). The stacking gel was 3% acrylamide (w/v), 0.125M Tris-HCl pH 6.8, 0.1% SDS (w/v), 2 mM EDTA, 0.2% TEMED (v/v), and 0.075% df ammonium persulfate (w/v). The electrode buffer consisted of 0.38M glycine, 0.1% SDS (w/v), 50 mM Tris, and 23 mM EDTA. The gels were fixed, stained with Coomassie Blue, and vacuum dried prior to autoradiography. In wheat germ cell free translations, all of the antisense RNAs inhibited translation of P3. The full-length antisense RNA, pGEMA3L, also reduced the amount of coat protein produced. A concentration-dependent effect was observed for the antisense RNA from pGEMA3L, such that as the amount of antisense RNA was increased, the level of P3 and coat protein translation decreased.

The extent of inhibition of P3 synthesis was dramatic; the P3 band was barely detectable even at an antisense RNA concentration of 20 ng/µl. The level of coat protein translation showed a more gradual decline with increasing amounts of pGEMA3L antisense RNA, and was still present at an antisense RNA concentration of 400 ng/µl. The antisense RNAs from pGEMA3M and pGEMA3S which both inhibit P3 translation, also had an effect on the translation of AMV coat protein; however, the effect was the opposite of that produced by antisense RNA from pGEMA3L.

N. tabacum var. Xanthi plants were grown from seed sterilized for 10 min. in 10% Clorox (v/v) and rinsed 3 times in sterile water. The seed was placed in Magenta boxes (Magenta Corporation, 3800 N. Milwaukee Ave., Chicago, Ill. 60641) on MX⁻ media containing 1 package of MS salts (Murashige and Skoog salts, Bigco), 0.5 mg thiamine, 0.5 mg pyridoxine, 0.5 mg nicotinic acid, 0.1 g myoinositol, 3% sucrose (w/v), 0.8% agar (w/v), brought to pH 5.8 with KOH in a final volume of 1 liter. The boxes were placed in a lighted culture room under 5–7 klux of light, 16 hr. per day at 28° C. to germinate. After 2–3 days, sets of true leaves developed, the top of the plantlet was cut off above the roots and placed on NA-1 media (identical to MX⁻ media except that 1 mg of kinetin is added per liter) in deep plastic petri dishes (100×25mm). Lighting and temperature conditions remained the same. Every 4 weeks, the shoots were subcultured by removal of the apical sections and placed on new NA-1 media.

At the time of subculture, shoots were also placed into Magenta boxes containing MX⁻ media. The boxes were kept in a lighted culture room under 3–5 klux of light, 16 hr. per day at 28° C. When the plantlets were about 4–5 weeks old, they were used for protoplast isolation.

Protoplast isolation was carried out as described by Nagata and Ishii (1979) Can. J. Bot. 57:1820–1823. Protoplasts were inoculated following protocols described by Samac et al. (1983) supra using 40% PEG-1540 (w/v) as the inoculating agent. Inoculated protoplasts were suspended in 1.0 ml of Aoki medium (Aoki and Takebe (1969) Virology 39:439–448) and incubated for 24 hr. Samples containing approximately 5×10⁴ protoplasts were pelleted and resuspended in 50 µl SDS sample buffer and run on gels as described above. Samples used to determine the percentage of infected protoplasts were fixed and stained with fluorescent antibody to the coat protein of AMV as described by Loesch-Fries and Hall (1980) J. Gen. Virol. 47:323–332. Procedures for immunoblots were similar to those described by Halk et (1986) Methods Enzymol. 118:766–780. Antibodies to a synthetic peptide consisting of the last 23 amino acids at the carboxy terminus of P3 and alkaline phosphatase-conjugated IgG (Sigma) were used to detect the 32K protein of AMV.

In protoplasts, each of the antisense RNAs reduced the percentage of protoplasts infected with AMV when either AMV RNA or AMV virions were used as the inoculum. The level of P3 detected in samples of infected protoplasts also decreased with increasing antisense RNA concentration. Antisense RNA from pGEMA3L had the greatest ability to reduce the percentage of AMV infected protoplasts and the detection of P3.

Alfalfa mosaic virus was isolated from infected Nicotiana tabacum var. Xanthi according to van Vloten-Doting and Jaspers (1972) Virology 48:699–708. Viral RNA was purified as described by Pinck and Hirth (1972) Virology 49:413–425.

In studies involving in vivo challenge of protoplasts with AMV RNA inoculum, each of the antisense RNAs had an effect not only on the amount of 32K protein detected in samples of infected protoplasts, but also on the percentage of infected protoplasts. As the concentration of any of the antisense RNAs in the inoculum was increased, the level of P3 detected in the infected protoplast samples was reduced. In addition, the percentage of infected protoplasts was also deceased by increasing the antisense RNA concentration in the inoculum (Table 1). For equivalent µg amounts of antisense RNA, the ability to reduce P3 translation and the percentage of infected protoplasts was: pGEMA3L>pGEMA3M>pGEMA3S, even though the molar ratio of these antisense RNAs is 1.0: 1.9: 7.7 respectively (Table 1).

TABLE 1

The effect of the antisense RNAs on the percentage of infected protoplasts.

| | % Infected Protoplasts |
|---|---|
| A) Infection with AMV RNA and pGEMA3-derived antisense RNA | |
| Mock | 0 |
| 5.0 μg AMV RNA (16 nmoles) | 66 |
| 5.0 μg AMV RNA + 2.0 μg pGEMA3S antisense (46 nmoles) | 56 |
| 5.0 μg AMV RNA + 5.0 μg pGEMA3S antisense (123 nmoles) | 49 |
| 5.0 μg AMV RNA + 10.0 μg pGEMA3S antisense (246 nmoles) | 17 |
| B) Infection with AMV RNA and pGEMA3M-derived antisense RNA | |
| Mock | 0 |
| 5.0 μg AMV RNA (16 nmoles) | 98 |
| 5.0 μg AMV RNA + 2.0 μg pGEMA3M antisense (11 nmoles) | 38 |
| 5.0 μg AMV RNA + 5.0 μg pGEMA3M antisense (29 nmoles) | 36 |
| 5.0 μg AMV RNA + 10.0 μg pGEMA3M antisense (58 nmoles) | 12 |
| C) Infection with AMV RNA and pGEMA3L-derived antisense RNA | |
| Mock | 0 |
| 5.0 μg AMV RNA (16 nmoles) | 88 |
| 5.0 μg AMV RNA + 2.0 μg pGEMA3L antisense (6 nmoles) | 14 |
| 5.0 μg AMV RNA + 5.0 μg pGEMA3L antisense (16 nmoles) | 4 |
| 5.0 μg AMV RNA + 10.0 μg pGEMA3L antisense (32 nmoles) | 1 |
| D) Infection with AMV virions and antisense RNA derived from pGEMA3S, pGEMA3M or pGEMA3l | |
| Mock | 0 |
| 5.0 μg AMV RNA (2.6 nmoles RNA) | 98 |
| 5.0 μg AMV virions + 5.0 μg pGEMA3S antisense (123 nmoles) | 75 |
| 5.0 μg AMV virions + 25.0 μg pGEMA3S antisense (615 nmoles) | 34 |
| 5.0 μg AMV virions + 5.0 μg pGEMA3M antisense (29 nmoles) | 87 |
| 5.0 μg AMV virions + 25.0 μg pGEMA3M antisense (145 nmoles) | 21 |
| 5.0 μg AMV virions + 5.0 μg pGEMA3L antisense (16 nmoles) | 79 |
| 5.0 μg AMV virions + 25.0 μg pGEMA3L antisense (78 nmoles) | 14 |
| 5.0 μg AMV virions + 25.0 μg E. coli tRNA | 91 |

The infectivity data were normalized in each experiment to take account the viability of the protoplasts.

One explanation for the results of antisense RNA effects on infection of protoplasts by RNA is that the antisense RNAs were able to hybridize to the AMV RNA in the inoculum, even though the RNAs were not specifically hybridized as in the in vitro translation studies. The resulting double stranded RNA outside the protoplasts may be much less infectious than the corresponding single stranded RNAs because of a reduced ability to enter the protoplasts. Thus, the antisense RNAs may be simply reducing the number of infectious RNA molecules outside of the protoplasts. In order to eliminate this possibility, AMV virions were also used as the inoculum (Table 1, D)). In the intact virion, AMV RNA is protected from hybridization to antisense RNA until the virions are uncoated inside the protoplasts.

When AMV virions were used in the inoculum, each of the antisense RNAs was still able to reduce the level of P3 detectable in the infected protoplasts. The level of P3 in infected protoplasts was reduced as the concentration of any of the antisense RNAs was increased. The percentage of infected protoplasts was also shown to decline as the concentration of antisense RNA in the inoculum was increased. This was true for all the antisense RNAs described, and the effect was most prominent with pGEMA3L (Table 1). As a control, E. coli tRNA was added to one of the protoplast samples to ensure that the effects described above were specific to the antisense RNAs studied. The non-complementary tRNA had no effect on either the level of P3 or the percentage of infected protoplasts (Table 1).

DISCUSSION OF RESULTS

The in vitro translation experiments, in which the effects of the three different antisense RNAs on the translation of AMV RNA were examined, confirmed that each of the antisense RNAs was capable of inhibiting the translation of AMV P3, and that the antisense RNA from pGEAM3L was also able to reduce the production of coat protein. It has been previously recognized (Pines and Inouye (1986) Trends Genet. 2(11):284–287) that antisense RNAs which are complementary to the 5' end of the mRNA and include the ribosome binding site are the most effective in preventing translation. Since all of the antisense RNA fragments are complementary to the 5' end of AMV RNA3, it appears that the mechanism of translation inhibition involves the interference of ribosome binding to the mRNA. Therefore, as the concentration of antisense RNA was increased relative to the mRNA concentration, it was expected that the antisense RNA would titrate out more and more of the mRNA available for ribosome binding and would result in a reduction of protein translation.

Addition of increasing amounts of antisense RNA from pGEMA3L, which is complementary to both RNA3 and RNA4, led to a rapid decline in the production of P3, and a more gradual decline in the amount of coat protein produced. The molar ratio of RNA4 in the AMV RNA preparations is higher than that of RNA3, and therefore, it was expected that the translation of coat protein RNA would decrease more gradually than the translation of P3 RNA with increasing amounts of pGEMA3L antisense RNA.

The in vivo studies, in which AMV RNA and each of the antisense RNAs were co-inoculated into protoplasts, showed that all of the antisense RNAs had an effect on the percentage of infected protoplasts and on the level of P3 protein detected in the protoplasts. It has not yet been determined whether the decrease in the percentage of infected protoplasts is a result of a reduction in the translation of P3, or whether the reduced level of P3 is due to the decline in the percentage of infected protoplasts. The reduction in the percentage of infected protoplasts by the addition of antisense RNA may be due to one or more of the following mechanisms. i) Each of the antisense RNAs have the potential to interfere with the replication of AMV. Antisense RNAs from pGEMA3M and pGEMA3S may not allow complete replication of AMV RNA3 because of their complementarity at the 5' end. ii) An inability of RNA3 to replicate may also result in a reduced production of the subgenomic RNA4 molecule, which could cause a decrease in the level of coat protein, iii) The 3' ends of each of the AMV RNAs have been shown to be homologous (Pinck and Pinck (1979) FEBS Lett. 107(1):61-65). Antisense RNA from pGEMA3L is complementary to the 3' ends of all of the AMV RNAs, which could interfere with the initiation of replication. Each of these mechanisms alone or in concert may be used to explain the observed decrease in the percentage of infected protoplasts in the presence of antisense RNA.

We claim:

1. A DNA molecule comprising, 5' to 3', a promoter region which functions in plants, a cDNA encoding AMV aRNA3 which has at least one deletion from the 3' end and not encoding AMV aRNA4, and a transcript terminator region capable of determining the 3' end of a transcript of said cDNA, wherein the promoter region is capable of causing transcription of said cDNA in a plant cell.

2. A DNA molecule according to claim 1 wherein the cDNA is pGEMA3M.

3. A DNA molecule according to claim 1 wherein the cDNA is pGEMA3S.

4. A DNA molecule according to claim 1 wherein the promoter is a CaMV 35 promoter.

5. A bacterial cell comprising the DNA molecule of claim 1.

6. A plant cell comprising the DNA molecule of claim 1.

7. A plant containing an incomplete AMV aRNA3 deleted from the 3' end whereby said plant is resistant to infection by AMV.

8. A DNA molecule comprising, 5' to 3', a promoter capable of initiating transcription in plant cells of a negative strand RNA complementary to a viral RNA, cDNA encoding aRNA of a plant virus having single-stranded, plus-stranded, tripartite RNA genome, and a transcript terminator capable of determining the 3' end of the transcript of said cDNA in a plant cell.

9. The DNA according to claim 8, wherein the cDNA is cDNA prepared from RNA4 of the plant virus.

10. The DNA according to claim 8, wherein the cDNA is cDNA to a virus of the alfalfa mosaic virus group.

11. The DNA according to claim 9, wherein the virus is AMV.

12. The DNA according to claim 11, wherein the virus is AMV strain 425.

13. The DNA according to claim 11, wherein the cDNA is AMV RNA1 cDNA.

14. The DNA according to claim 11, wherein the cDNA is AMV RNA2 cDNA.

15. The DNA according to claim 11, wherein the cDNA is AMV RNA3 cDNA.

16. The DNA according to claim 11, wherein the cDNA is AMV RNA4 cDNA.

17. The DNA according to claim 8, wherein the aRNA is complementary to a viral translational initiation site.

18. The DNA according to claim 8, wherein the aRNA is complementary to a viral 5'-untranslated sequence between a cap site and translational start site of an mRNA of said virus.

19. The DNA according to claim 8, wherein the aRNA is complementary to a viral 3'-conserved sequence, which is conserved in all genomic components of a tripartite RNA viral genome.

20. The DNA according to claim 8, wherein, with the exception of no more than five nucleotides at either end of the molecule, the cDNA is complementary to an entire mRNA of a plant virus.

21. The DNA according to claim 8, wherein the promoter is a CaMV 19S promoter.

22. The DNA according to claim 8, wherein the transcript terminator is a polyadenylation site.

23. The DNA according to claim 22, wherein the polyadenylation site is a CaMV polyadenylation site.

24. The DNA according to claim 8, further comprising a plant-expressible marker selected from the group consisting of selectable and screenable markers.

25. The DNA according to claim 24, wherein the selectable marker encodes neomycin phosphotransferase.

26. The DNA according to claim 24, wherein the marker further comprises an ocs gene.

27. The DNA according to claim 26, wherein the DNA further comprises T-DNA of pH400.

28. The DNA according to claim 27, wherein the DNA is pH400A4I.

29. A bacterial cell comprising the DNA of claim 8.

30. The DNA according to claim 8, wherein the region of the molecule containing the promoter, the cDNA, and the terminator are flanked by plant DNA.

31. A plant cell comprising the DNA of claim 8.

32. The plant cell according to claim 31, wherein the plant virus is of the alfalfa mosaic virus group.

33. The plant cell according to claim 32, wherein the plant virus is AMV.

34. The plant cell according to claim 33, wherein the plant virus is AMV strain 425.

35. The method for producing a virus-resistant plan cell, wherein the method comprises the steps of:
(a) preparing a DNA molecule according to claim 8 which encodes an aRNA of a plant virus having a single-stranded, plus-stranded, tripartite RNA genome;
(b) ligating the cDNA segment downstream from a promoter DNA segment, wherein the promoter is capable of initiating transcription of the aRNA in a plant cell; and
(c) transforming a transformable, regenerable plant cell to contain the ligated DNA molecule of step (b).

36. The method according to claim 35, wherein the cDNA is a cDNA to RNA4.

37. The method according to claim 36, wherein the cDNA is a cDNA to a virus of the alfalfa mosaic virus group.

38. The method according to claim 37, wherein the virus is AMV.

39. The method according to claim 38, wherein the virus is AMV strain 425.

40. The method according to claim 38, wherein the cDNA is AMV RNA1 cDNA.

41. The method according to claim 38, wherein the cDNA is AMV RNA2 cDNA.

42. The method according to claim 38, wherein the cDNA is AMV RNA3 cDNA.

43. The method according to claim 38, wherein the cDNA is AMV RNA4 cDNA.

44. The method according to claim 35, wherein the aRNA is complementary to a viral translational initiation site.

45. The method according to claim 35, wherein the aRNA is complementary to a viral 5'-untranslated sequence between a cap site and a translational start site of an mRNA of said virus.

46. The method according to claim 35, wherein the aRNA is complementary to a viral 3'-conserved sequence, which is conserved in all genomic components of a tripartite RNA viral genome.

47. The method according to claim 35, wherein, with the exception of no more than five nucleotides at either end of the molecule, the cDNA is complementary to an entire mRNA of a plant virus.

48. The method according to claim 35, wherein the DNA molecule further comprises a plant-expressible marker selected from the group consisting of selectable and screenable markers.

49. The method according to claim 48, wherein the selectable marker encodes neomycin phosphotransferase.

50. The method according to claim 48, further comprising the step of culturing the plant cells in the presence of a selective agent to which the selectable marker confers resistance.

51. The method according to claim 50, wherein the selective agent is selected from the group consisting of kanamycin and an analog thereof.

52. The method according to claim 51, wherein the DNA further comprises ocs.

53. The method according to claim 52, further comprising the step of culturing the plant cell in the presence of aminoethyl cysteine.

54. The method according to claim 52, wherein the DNA further comprises pH400.

55. The method according to claim 54, wherein the DNA is pH400A4I.

56. A virus-resistant plant cell produced by the method of claim 35.

57. A virus-resistant plant cell descended from the plant cell of claim 56.

58. A virus-resistant plant containing the DNA molecule of claim 8.

59. A plant seed produced from the virus-resistant plant of claim 57.

60. A method for inhibiting viral infection in a plant by an RNA virus, wherein the method comprises:
(a) transforming a plant cell with the DNA according to claim 8, wherein the DNA when transcribed results in a negative strand RNA which is complementary to a viral RNA sequence; and
(b) regenerating plants from said cell to produce a plant having cells in which said complementary sequence is transcribed providing protection against viral disease symptoms.

* * * * *